(12) United States Patent
Owen et al.

(10) Patent No.: US 9,734,986 B2
(45) Date of Patent: *Aug. 15, 2017

(54) MINERAL IDENTIFICATION USING SEQUENTIAL DECOMPOSITION INTO ELEMENTS FROM MINERAL DEFINITIONS

(71) Applicant: FEI Company, Hillsboro, OR (US)

(72) Inventors: Michael James Owen, Geebung (AU); Michael Buhot, Brisbane (AU)

(73) Assignee: FEI Company, Hillsboro, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/728,751

(22) Filed: Jun. 2, 2015

(65) Prior Publication Data

US 2015/0338358 A1    Nov. 26, 2015

Related U.S. Application Data

(63) Continuation of application No. 13/661,830, filed on Oct. 26, 2012, now Pat. No. 9,048,067.

(51) Int. Cl.
| | | |
|---|---|---|
| *H01J 37/00* | (2006.01) | |
| *H01J 37/252* | (2006.01) | |
| *G01N 23/225* | (2006.01) | |

(52) U.S. Cl.
CPC ........ *H01J 37/252* (2013.01); *G01N 23/2252* (2013.01); *H01J 2237/221* (2013.01); *H01J 2237/24585* (2013.01); *H01J 2237/2561* (2013.01)

(58) Field of Classification Search
CPC .............. H01J 37/252; H01J 2237/221; H01J 2237/2237; H01J 2237/24585; H01J 2237/2561; G01N 23/2252

USPC ................ 250/306, 307, 309, 310, 311, 305
See application file for complete search history.

(56) References Cited

U.S. PATENT DOCUMENTS

| | | | |
|---|---|---|---|
| 4,037,101 A | 7/1977 | Okumura et al. | |
| 4,136,429 A | 1/1979 | Brandes | |
| 4,242,586 A | 12/1980 | Warble | |
| 4,435,507 A | 3/1984 | Stenkvist | |
| 4,476,386 A | 10/1984 | Reid et al. | |
| 4,587,424 A | 5/1986 | Grau | |
| 4,592,082 A | 5/1986 | Pawloski | |
| 4,807,148 A | 2/1989 | Lacey | |
| 4,834,943 A | 5/1989 | Yoshiyama | |
| 4,839,516 A | 6/1989 | Freeman et al. | |
| 5,084,618 A | 1/1992 | Ito | |
| 5,555,198 A | 9/1996 | Asano | |
| 5,741,707 A | 4/1998 | Herron et al. | |
| 5,798,525 A | 8/1998 | Benizri-Carl et al. | |
| 5,866,903 A | 2/1999 | Morita et al. | |
| 5,906,919 A | 5/1999 | Garini et al. | |

(Continued)

*Primary Examiner* — Wyatt Stoffa
*Assistant Examiner* — Hanway Chang
(74) *Attorney, Agent, or Firm* — Scheinberg & Associates, P.C.; John B. Kelly; Michael O. Scheinberg

(57) ABSTRACT

Mineral definitions each include a list of elements, each of the elements having a corresponding standard spectrum. To determine the composition of an unknown mineral sample, the acquired spectrum of the sample is sequentially decomposed into the standard spectra of the elements from the element list of each of the mineral definitions, and a similarity metric computed for each mineral definition. The unknown mineral is identified as the mineral having the best similarity metric.

19 Claims, 25 Drawing Sheets

(56) References Cited

U.S. PATENT DOCUMENTS

| | | |
|---|---|---|
| 5,991,028 A | 11/1999 | Cabib et al. |
| 6,018,587 A | 1/2000 | Cabib |
| 6,066,459 A | 5/2000 | Garini et al. |
| 6,072,178 A | 6/2000 | Mizuno |
| 6,093,930 A | 7/2000 | Boyette, Jr. et al. |
| 6,122,343 A | 9/2000 | Pidcock |
| 6,140,643 A | 10/2000 | Brown et al. |
| 6,282,301 B1 | 8/2001 | Haskett |
| 6,341,257 B1 | 1/2002 | Haaland |
| 6,377,652 B1 | 4/2002 | Sturm |
| 6,466,929 B1 | 10/2002 | Brown et al. |
| 6,470,335 B1 | 10/2002 | Marusak |
| 6,584,413 B1 | 6/2003 | Keenan et al. |
| 6,658,143 B2 | 12/2003 | Hansen et al. |
| 6,674,894 B1 | 1/2004 | Parker et al. |
| 6,687,620 B1 | 2/2004 | Haaland et al. |
| 6,711,503 B2 | 3/2004 | Haaland |
| 6,723,871 B2 | 4/2004 | Tada et al. |
| 6,724,940 B1 | 4/2004 | Qian et al. |
| 6,765,205 B2 | 7/2004 | Ochiai et al. |
| 6,842,702 B2 | 1/2005 | Haaland et al. |
| 6,888,920 B2 | 5/2005 | Blank et al. |
| 6,993,170 B2 | 1/2006 | Johnson et al. |
| 7,053,365 B2 | 5/2006 | Shimomura |
| 7,061,605 B2 | 6/2006 | Lemmo et al. |
| 7,108,970 B2 | 9/2006 | Levinson |
| 7,132,652 B1 | 11/2006 | Testoni |
| 7,139,415 B2 | 11/2006 | Finkbeiner |
| 7,161,672 B2 | 1/2007 | Gornushkin et al. |
| 7,243,030 B2 | 7/2007 | Reeve et al. |
| 7,400,770 B2 | 7/2008 | Keaton et al. |
| 7,436,510 B2 | 10/2008 | Grun et al. |
| 7,462,819 B2 | 12/2008 | Smart et al. |
| 7,490,009 B2 | 2/2009 | Gottlieb et al. |
| 7,790,465 B2 | 9/2010 | Otvos |
| 7,804,059 B2 | 9/2010 | Harrison |
| 7,930,106 B2 | 4/2011 | Carrick |
| 7,979,217 B2 | 7/2011 | Gottlieb et al. |
| 8,060,173 B2 | 11/2011 | Goode, Jr. et al. |
| 8,119,991 B2 | 2/2012 | Harrison |
| 8,233,667 B2 | 7/2012 | Helgason et al. |
| 8,515,008 B2 | 8/2013 | Ullberg et al. |
| 2004/0011958 A1 | 1/2004 | Wright et al. |
| 2004/0027350 A1 | 2/2004 | Kincaid et al. |
| 2004/0147830 A1 | 7/2004 | Parker et al. |
| 2005/0037515 A1 | 2/2005 | Nicholson et al. |
| 2005/0060868 A1 | 3/2005 | McMurtry |
| 2005/0165290 A1 | 7/2005 | Kotsianti et al. |
| 2006/0051251 A1 | 3/2006 | Desrosiers et al. |
| 2006/0291619 A1 | 12/2006 | Statham |
| 2007/0137823 A1* | 6/2007 | Haran ............... 162/198 |
| 2008/0250881 A1 | 10/2008 | Dona |
| 2009/0306906 A1* | 12/2009 | Gottlieb et al. ........ 702/30 |
| 2010/0060893 A1 | 3/2010 | Norton et al. |
| 2011/0144922 A1 | 6/2011 | Corbett et al. |
| 2013/0015351 A1 | 1/2013 | Kooijman et al. |
| 2013/0134307 A1 | 5/2013 | Routh, Jr. |

\* cited by examiner

MINERAL IDENTIFICATION USING SEQUENTIAL DECOMPOSITION INTO ELEMENTS FROM MINERAL DEFINITIONS

TECHNICAL FIELD OF THE INVENTION

The present invention relates generally to methods and structures for identifying minerals using charged particle beam systems and x-ray spectroscopy systems.

BACKGROUND OF THE INVENTION

Mineral analysis systems, such as the QEMSCAN® (Quantitative Evaluation of Minerals by Scanning electron microscopy) and MLA® (Mineral Liberation Analyzer) both from FEI Company, the assignee of the present invention, have been used for many years to analyze samples from mines to determine the presence of valuable minerals. Such systems direct an electron beam toward the sample and measure the energy of x-rays coming from the material in response to the electron beam for elemental analysis or chemical characterization of a sample. One such process is called "energy dispersive x-ray analysis" or "EDS."

EDS systems rely on the emission of X-rays from a sample to perform elemental analysis. Each element has a unique atomic structure, which produces x-rays that are characteristic of an element's atomic structure, thereby allowing the element to be uniquely identified by its x-ray spectrum. To stimulate the emission of x-rays from a sample, a beam of charged particles is focused onto the sample, which causes electrons from inner shells to be ejected. Electrons from outer shells drop to the inner shells to fill this electron void, and the difference in energy between the higher energy shell and the lower energy shell is released as an x-ray, which can be measured by an EDS detector.

Backscattered electron (BSE) detectors are also used for mineral analysis in conjunction with electron beam columns. The intensity of the BSE signal is a function of the average atomic number of the material under the electron beam, and this relationship can be used to develop a useful mineral identification method.

The QEMSCAN and MLA both comprise an SEM, one or more EDS detectors, a BSE detector, and software for controlling automated data acquisition and analysis. The QEMSCAN system identifies and quantifies elements within an acquired spectrum. This process is known as "elemental decomposition" because the spectrum is "decomposed" into spectra of individual elements. The elements found in the decomposition may then be compared with "mineral definitions," which specify criteria that must be met to identify the elements with a particular mineral. A mineral definition may include fixed ranges of the elemental proportions. For example, a QEMSCAN mineral definition may define a sample to be quartz if the EDS analysis shows a silicon proportion of between 45% and 47% and an oxygen proportion of between 52% and 55%.

The widths of the ranges in the mineral definitions are functions not only of variability in the composition of the mineral, but also of the accuracy of the measurement. The widths of the x-ray peaks depend directly on the number of x-rays measured, which defines the quality of the spectrum. A range width used in a mineral definition is determined for a spectrum having a specific number of x-rays; the same width cannot be applied to higher or lower quality spectrum composed of more or fewer x-rays. Thus, it is not possible to define a universal rules database for an arbitrary number of X-ray counts using the QEMSCAN.

This approach becomes increasingly difficult as fewer x-ray counts are used, because the signal-to-noise ratio drops below the point where discrimination between certain elements is possible. For example, Na and Zn have a very similar peak in an x-ray spectrum around 1 keV. Zn has another peak at 8.6 keV. If the concentration of Zn is low, the second x-ray peak becomes indistinguishable from the background, and as a result, identifying whether an x-ray spectrum contains Na or Zn becomes difficult. Because it can be difficult to identify individual elements, the mineral definitions being matched may have to be sufficiently flexible to accommodate elements that are not in the mineral, but that can be misidentified for elements in the mineral.

Moreover, the QEMSCAN indicates a match as either true or false, without considering how well the unknown spectrum matches a standard spectrum for a mineral. The system picks the first match it finds, even if a better match might be present elsewhere in the mineral database.

MLA, on the other hand, compares a measured mineral spectrum with known mineral spectra from a library and computes a probability match between a measured mineral spectrum and a reference mineral spectrum. This method works well, but the probability value obtained tends to be dominated by the size of the largest peak in the x-ray spectrum.

A BSE detector provides additional information about a mineral and can assist in identification of an unknown sample. The acquisition time of a suitable BSE signal is typically on the order of microseconds per pixel, while EDS systems have a longer acquisition time, typically requiring several seconds per pixel to obtain a spectrum adequate to be differentiated from all other mineral spectra. Unlike a BSE detector, EDS systems are typically insensitive to light atoms. BSE data may be useful for differentiating between minerals composed of the same elements, but in different proportions. For such minerals, the average atomic weight which determines the BSE intensity, will be different, while the elemental spectra will be similar. Because both EDS detectors and BSE detectors each have advantages, it is sometimes useful to use both BSE and x-ray spectra to accurately identify a mineral. Using both signals, however, requires more analysis time, which may not be available in commercial applications.

A mineral classification system should, like the MLA, be capable of comparing each unknown measured spectrum to a library of known mineral spectrums, and then making a selection based on which known mineral is most similar to the measured spectrum.

To compare spectra, the similarity of two spectra is typically reduced to a single number, a similarity metric. The single number quantifies similarity so that it is possible to determine which of two spectra is more similar to a third spectrum. A spectrum may be considered as a histogram showing the number of x-rays detected at various energy ranges, referred to as "channels." One similarity metric is the sum over the energy channels of the differences between the two normalized spectrums. Another similarity metric is a calculated probability that the unknown mineral is composed of the mineral defined by the mineral definition. The MLA uses a chi-squared probability statistic as a similarity metric to compare the value at each energy channel of the measured spectrum to the value at the corresponding channel of the known mineral spectrum. A problem of using a comparison on a channel-by-channel basis is that there is no guarantee that all required peaks in the mineral spectrum are present in the measured spectrum. It is possible that a measured spectrum appears to be similar to a mineral yet it is missing an element that is required by the definition of that mineral. The measured spectrum may also have an additional element not found in that definition of a mineral.

FIG. 1 provides an example of a prior art mineral comparison spectrum 100 containing an unknown measured spectrum 102 and a defined mineral spectrum 104. In this particular case, the defined mineral spectrum 104 is that of the mineral dolomite. Using a prior art comparison mechanism that calculate a probability directly from the spectrums, the unknown measured spectrum 102 produces a maximum similarity of 97% with the dolomite definition spectrum 104. This 97% similarity would indicate a very close match of the spectrums. However, the unknown spectrum 102 clearly contains an additional element at approximately 175 keV that is not found in dolomite. This misclassification would likely go undetected without significant quality assurance performed by the operator of the software.

Another difficulty with current mineral identification systems is that, many minerals are as non-stoichiometric mixtures. Such minerals may have a range of elemental proportions, rather than always appearing with the same proportion of each element. In the prior art, this was typically ignored, and each mineral defined as having a specific proportion of elements, leading to misidentification of minerals.

Thus, there is a need for an improved mineral identification method.

SUMMARY OF THE INVENTION

An object of the invention is to improve mineral identification.

Embodiments of the invention use a charged particle beam system with an x-ray spectroscopy system to detect characteristic x-rays and identify minerals. In some embodiments, a mineral database with improved mineral definitions is provided, along with an improved method to compute a match between a measured sample and the mineral definitions in this database.

In some embodiments, mineral definitions may include a range of elemental compositions, and these definitions can be used to identify minerals using a similarity measure that accounts for the variability of the mineral definition. In some embodiments, a measure of variability is derived from a high quality spectrum composed of hundreds of thousands or millions of x-ray counts. The variability of a spectrum composed of a smaller number of x-ray counts can then be calculated and used to determine a similarity metric between a standard spectrum and the unknown spectrum composed of fewer x-ray counts.

In some embodiments, a mineral in an unknown spectrum is identified by decomposing the unknown spectrum into the elements listed in each mineral definition in a mineral list, and then choosing the mineral definition that matches best and meets a minimum threshold.

The various improvements described herein can be implemented separately in mineral identification systems or may be combined.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Figure 1:
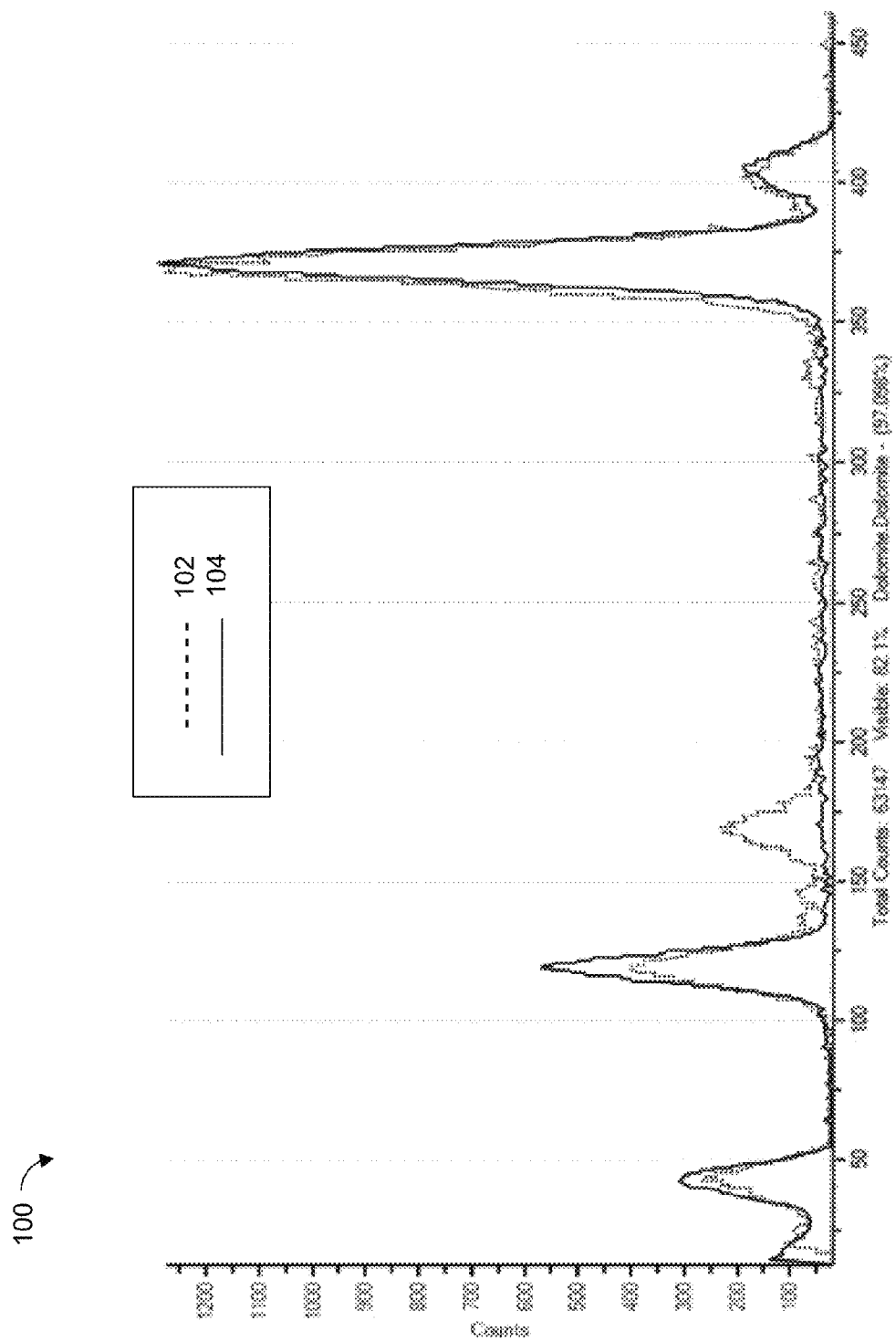
FIG. 1 is an example of a prior art mineral comparison spectrum containing an unknown measured spectrum and a defined mineral spectrum.

Several of the techniques described herein are separately novel and may be used independently or together.

In some embodiments, mineral identification is improved by comparing the unknown spectrum to the element list in each of multiple definitions. A similarity metric is determined for each mineral definition, and the unknown mineral is identified with the mineral definition having the best similarity metric that exceeds a threshold. That is, rather than trying to match the unknown spectrum with a combination of all possible elemental spectra, the unknown spectrum is matches with only those elements in the mineral definition, one mineral definition at a time In some embodiments, mineral identification is improved by using mineral definitions that include a mean and a variation measure for the relative quantity of each element in the mineral, and/or for some other measured value, such as atomic weight, of the mineral. A similarity metric, such as a match probability, can then be calculated for an unknown spectrum having any number of x-ray counts (or other measured value) by using the mean and variation from the definition, with the expected variation of the low count sample x-ray count being determined from the large-sample variation in the mineral definition. The mineral definition may comprise, for example, a high-count x-ray spectrum (greater than about 100,000 counts), a mean atomic number from back-scattered electron data (e.g., 50), the elemental composition of the mineral (e.g., Fe: 91%, O: 16%), and measures of variability of the compositional and/or the atomic number values. The mineral definition database can also contain other types of measurement data, such as electroluminescent data, as available. Applicants note that the relative quantities of elements in a mineral definition are not constrained to add to 100% because they may not represent elemental weight percentages.

In some embodiments, a mineral definition includes a range for one or more values, instead of a single value. For example, the atomic number of the mineral or the relative quantity of elements may be defined by ranges. In an example of a mineral definition having only two elements, the mineral definition can be shown as a line segment on a graph, with each axes of the graph representing the mineral concentration between 0% and 100%, and the end points of the line segment representing the boundaries of the concentration permitted under the mineral definition. A similarity metric can comprises the shortest distance from the measured elemental composition to the line segment. The similarity metric may comprise a projection of the measured point onto the line containing the line segment, and, if the projection is outside the line segment, the similarity metric may be the distance from the measured point to the nearest end point of the line segment. Alternatively, the line segment may be extended if the distance between the datapoint representing the unknown mineral and the endpoint is sufficiently short. While explained above in two dimensions for a mineral definition having two elements, the concept is extendable to additional elements by using additional dimensions, with the mineral definition defined as a subspace of the space of all possible combinations of the multiple elements in the mineral definition. The similarity metric can then be related to a projection of the point representing the unknown mineral onto the multidimensional subspace. If the projection falls outside of the subspace, the similarity metric is computed from the closest end or edge point in the subspace. The multi-dimension subspace can be defined by end member mineral compositions.

Figure 2:
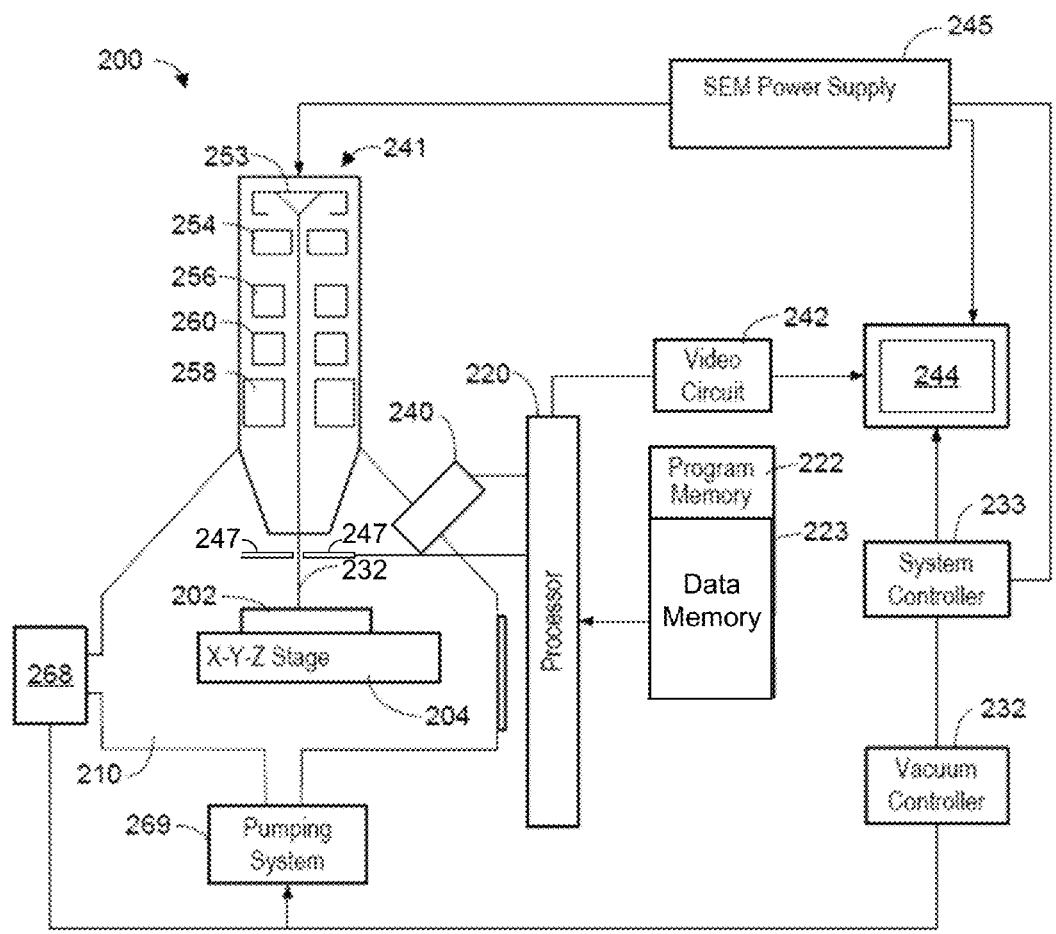
FIG. 2 is an example of a scanning electron beam system with an x-ray detector suitable for analyzing samples prepared according to the present invention.

FIG. 2 is an example of a mineral identification system 200 that includes a scanning electron beam system 241 including an x-ray detector 240 suitable for analyzing samples. An electron beam 232 is emitted from a cathode 253 by applying voltage between cathode 253 and an anode 254. Electron beam 232 is focused to a fine spot by means of a condensing lens 256 and an objective lens 258. Electron beam 232 is scanned two-dimensionally on the specimen by means of a deflection coil 260. Operation of condensing lens 256, objective lens 258, and deflection coil 260 is controlled by power supply and control unit 245.

A system controller 233 controls the operations of the various parts of the system 200, including on SEM power supply unit and control unit 245 that controls the operation of SEM 241. The vacuum chamber 210 is evacuated by mechanical pumping system 269 and ion pump 268 under the control of vacuum controller 232.

Electron beam 232 can be focused onto sample 202, which is on movable X-Y stage 204 within lower vacuum chamber 210. When the electrons in the electron beam strike sample 202, the sample gives off x-rays whose energy correlated to the elements in the sample. X-rays having energy inherent to the elemental composition of the sample are produced in the vicinity of the electron beam incident region. Emitted x-rays are collected by x-ray detector 240, preferably an energy dispersive detector of the silicon drift detector type, although other types of detectors could be employed, which generates a signal indicative of the energy of the detected x-ray.

Output from detector 240 is amplified and sorted by the processor 220, which counts and sorts the total number of X-rays detected during a specified period of time, at a selected energy and energy resolution, and a channel width (energy range) of typically between 10-20 eV per channel. System 200 also includes a display 244 for displaying the results of the mineral analysis and other information by way of video circuit 242; a program memory 222 for storing executable computer program code and a data memory 223 for storing data, such as measured spectra, standard spectra, backscatter electron data, diffraction patterns of materials, etc.

Processor 220 can be a part of a standard laboratory personal computer, and is typically coupled to at least some form of computer-readable media. Computer-readable media, which include both volatile and nonvolatile media, removable and non-removable media, may be any available medium that can be accessed by processor 220. By way of example and not limitation, computer-readable media comprise computer storage media and communication media. Computer storage media include volatile and nonvolatile, removable and non-removable media implemented in any method or technology for storage of information such as computer-readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 220.

Program memory 222 can include computer storage media in the form of removable and/or non-removable, volatile and/or nonvolatile memory and can provide storage of computer-readable instructions, data structures, program modules and other data. Generally, the processor 220 is programmed by means of instructions stored at different times in the various computer-readable storage media of the computer. Programs and operating systems are typically distributed, for example, on floppy disks or CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described below in conjunction with a microprocessor or other data processor. The invention also includes the computer itself when programmed according to the methods and techniques described herein.

While the embodiment shown includes a scanning electron microscope, related embodiment could use a transmission electron microscope or a scanning transmission electron microscope to generate x-rays from the sample. An x-ray fluorescence system could also be used to generate x-rays from the sample. Other embodiments may detect other characteristic radiation, such as gamma rays, from a sample.

Calculation of a Similarity Metric

In some embodiments, part of comparing an unknown spectrum with a mineral definition includes calculating a similarity metric. The value calculated for the similarity metric will vary with the number of x-ray counts used to measure the unknown sample.

One of the difficulties of mineral identification is that a precise spectrum requires a very long acquisition time. A decrease in total X-ray count results in a decreased acquisition time, but reduces the signal-to-noise ratio. Some embodiments of the present invention allow a decreased acquisition time while maintaining high identification accuracy by using the x-ray count as a parameter to determine an overall probability that a mineral definition matches a measured spectrum. The standard deviation of the spread at different x-ray counts can also be modeled and used as a part of the identification algorithm.

Figure 3A:
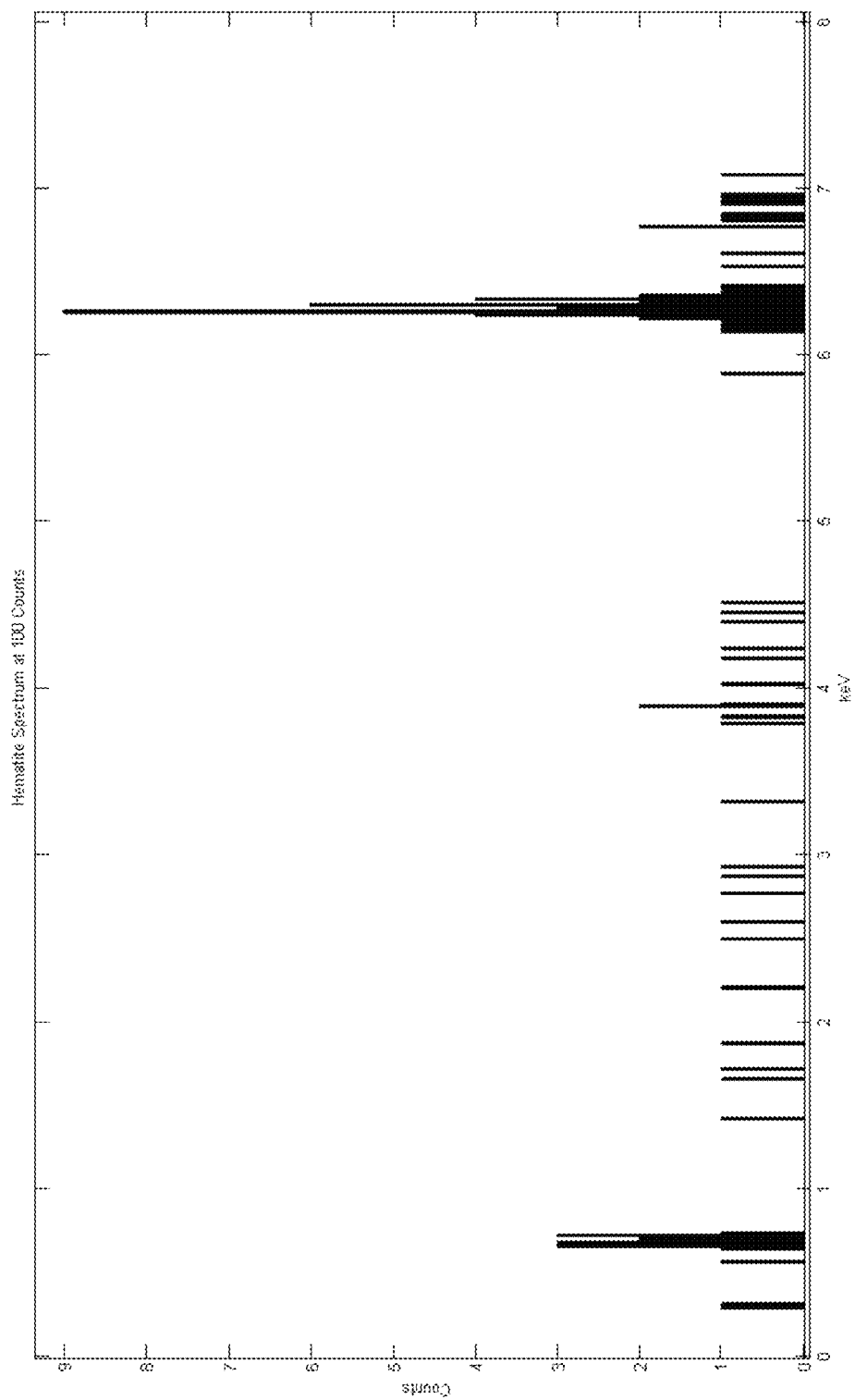
FIGS. 3A-3C shows example spectra of hematite ($Fe_2O_3$) obtained using different numbers of x-ray counts.
Figure 3B:
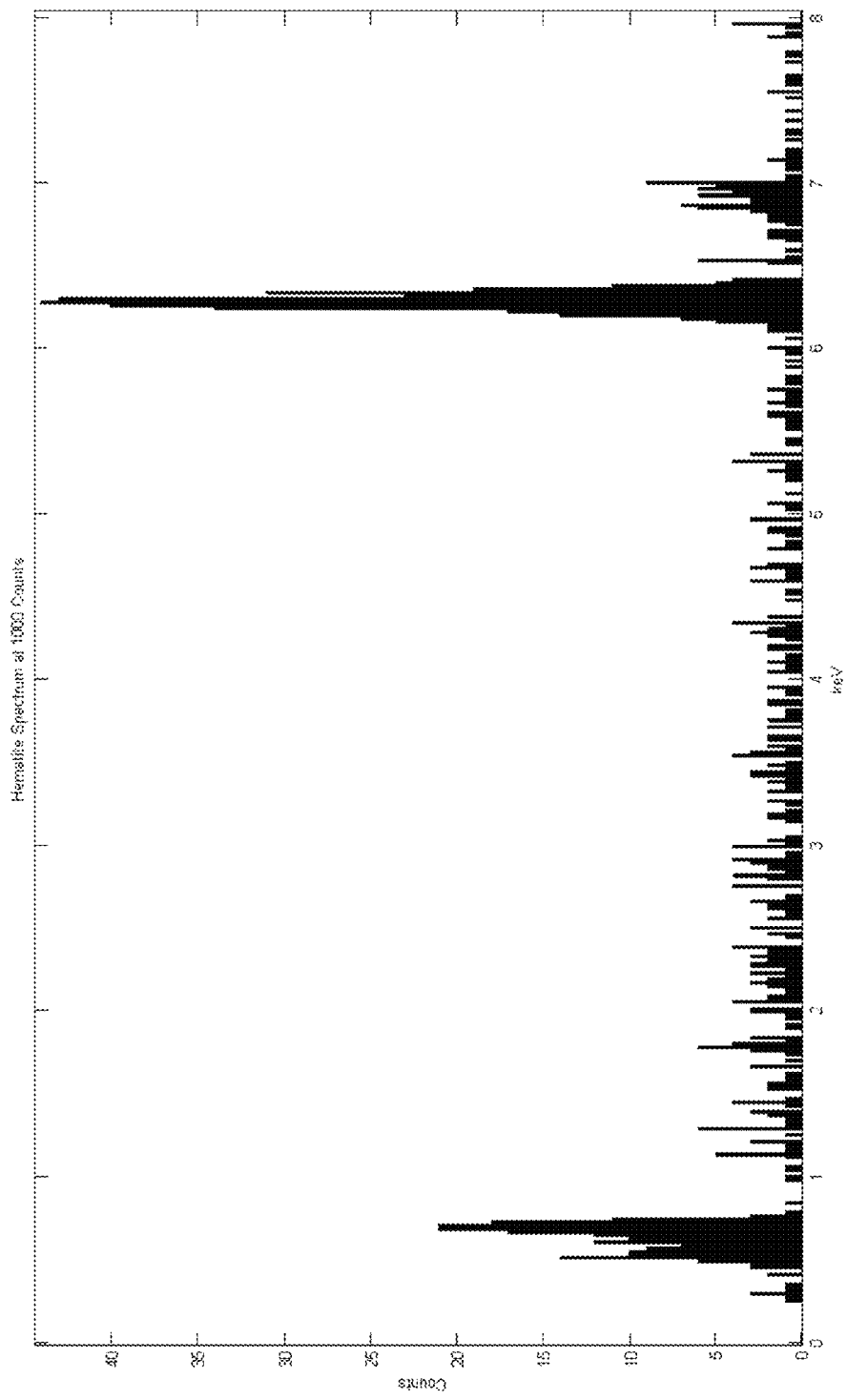
Figure 3C:
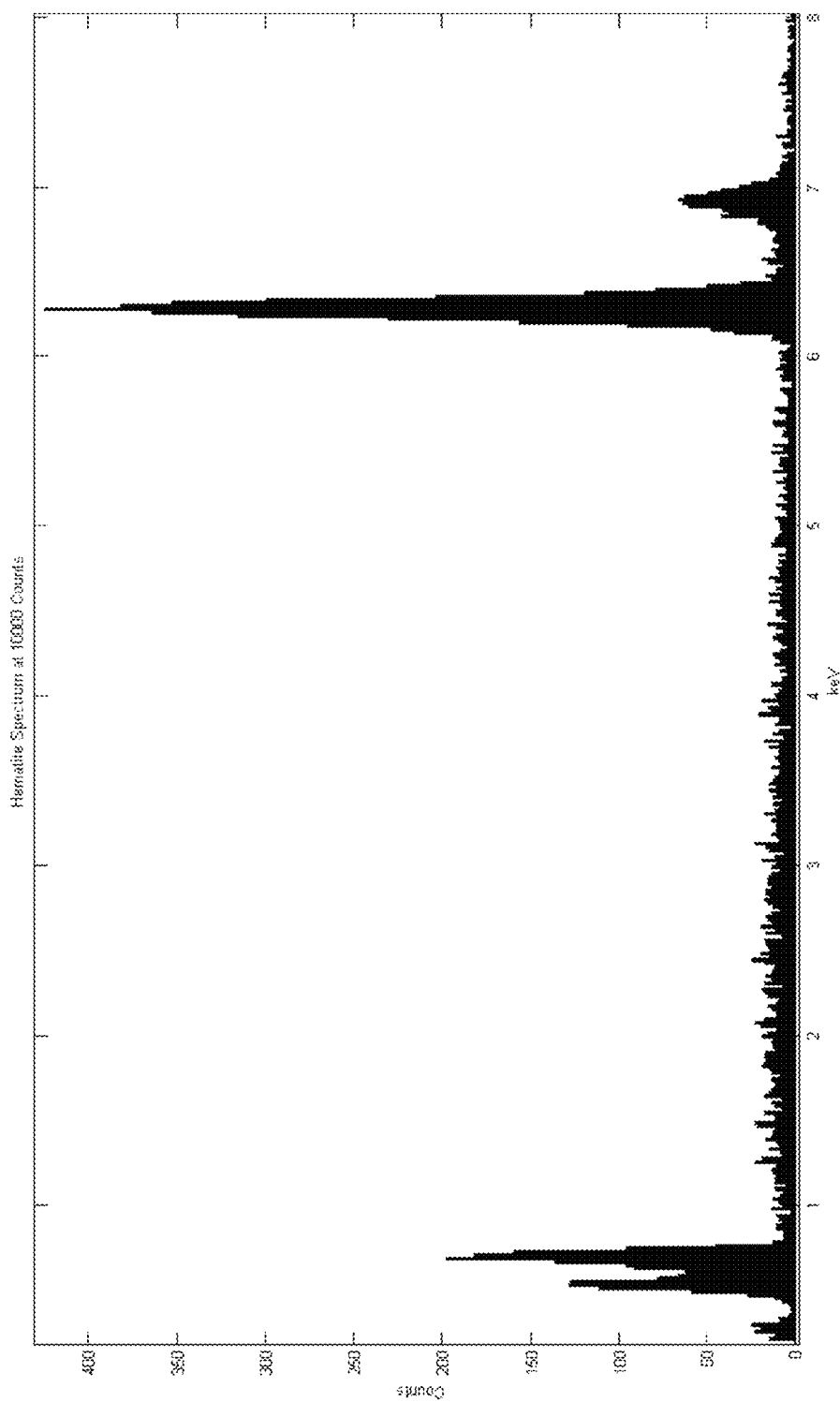

There is an expected error in the determination of the proportion of elements in a sample, and the size of the error depends on the number of x-ray counts in the spectra. The more x-ray counts, the more accurately the peaks are located and the more accurate the quantitative analysis of the relative peak heights to determine the relative proportion of elements. FIGS. 3A-3C shows example spectra of hematite ($Fe_2O_3$) derived from 100, 1000, and 10000 counts, respectively. The x-axis is the x-ray energy in keV and the y-axis shows the number of x-rays detected at each energy level. The peak around 6.9 keV, for example, is barely discernible in FIG. 3A, but is apparent in FIG. 3C.

Figure 4:
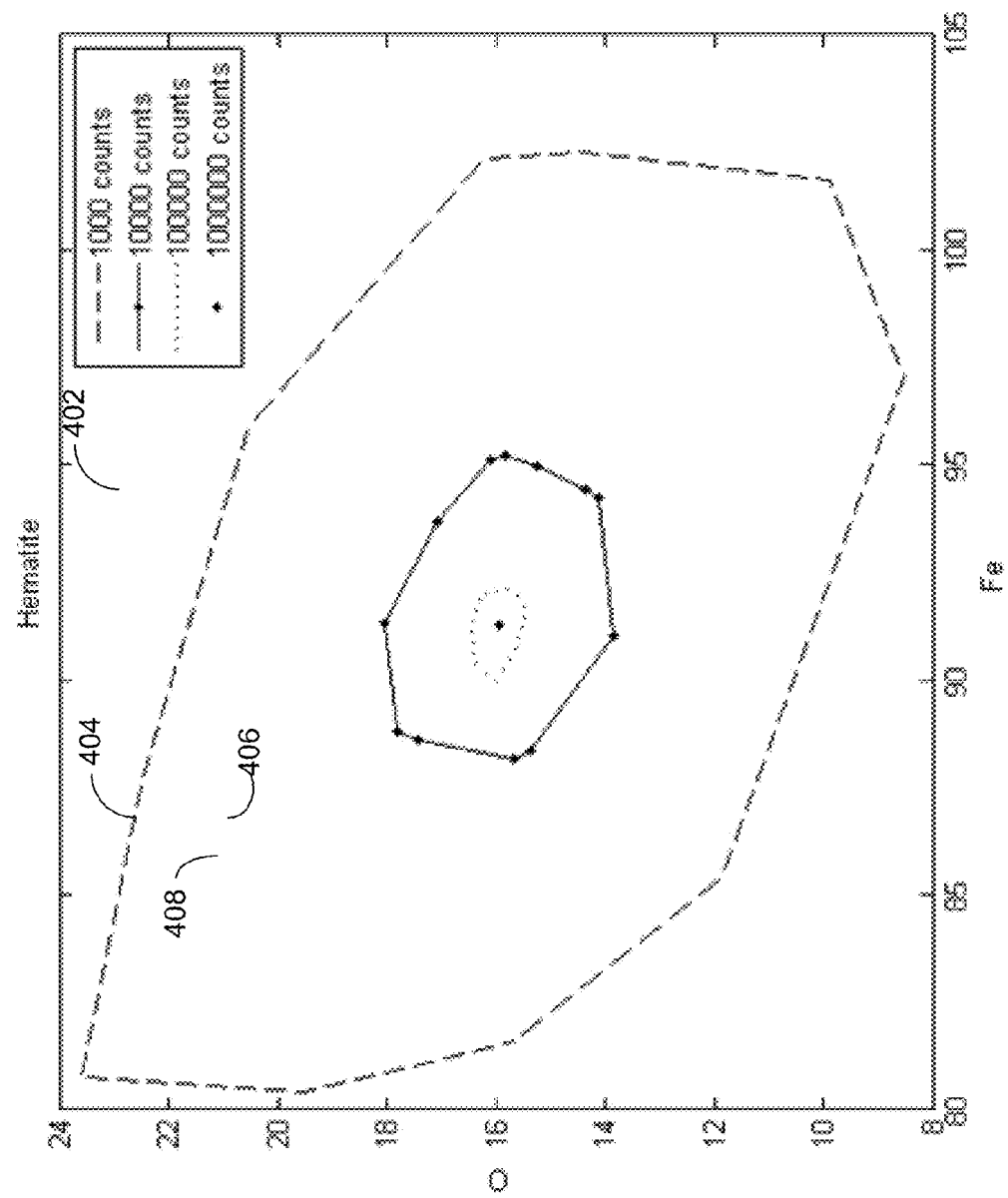
FIG. 4 shows scatter plots indicating the proportion and spread of Fe and O calculated from x-ray spectrums at different counts.

FIG. 4 shows a scatter plot showing the proportion Fe and O calculated from measurements using different numbers of x-ray counts. To obtain this type of scatter plot, multiple x-ray spectra of hematite are acquired and decomposed into elemental concentrations. The region enclosed by each line represents the spread of elemental concentrations found at the specified number of x-ray counts. Because of the measurement error, the calculated values of the percentage of Fe and O were different for different measurements. Plots 402, 404, 406, and 408 show the expected variation in measured elemental quantity in hematite spectrums at 1000, 10000, 100000, and 1000000 counts, respectively. Plot 402, which corresponds to the lowest count spectra (1000 counts), shows a much larger variation in the computed quantities of iron and oxygen. Some embodiments of the invention use the number of x-ray counts as a parameter in determining a similarity metric, such as a probability of a match. For example, elemental decomposition of an a spectrum showing 94% iron and 16% oxygen could be a match for hematite if the spectrum was composed of 10,000 counts, but not if the spectrum was composed of 100,000 because the 100,000 spectrum is expected to be more accurate and produce a result closer to actual value.

Some embodiments of the invention comprises defining a mineral in terms of an attribute value and a variability, for example, relative elemental quantities and standard deviations of these quantities. The variability of the elemental quantity is a function of the number of X-ray photons collected. A probability or other similarity metric that an observed value matches the definition of a mineral is then computed. As shown in FIG. 4, when a smaller number of photons is collected, the computed definitional range for the mineral definition is larger, due to the increased variation in the measurement.

Figure 5:
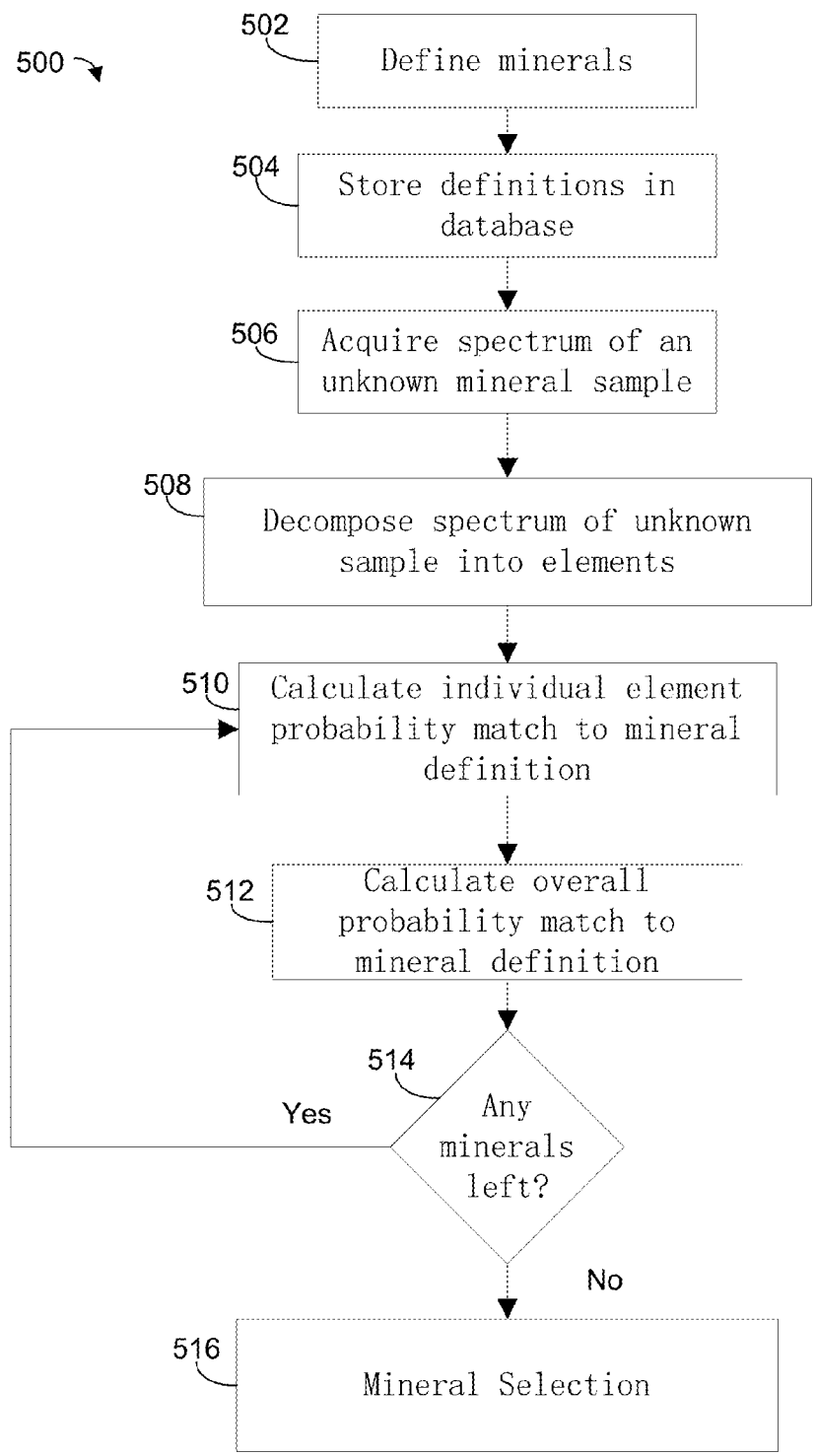
FIG. 5 is a flowchart illustrating the process of identifying an unknown mineral sample according to an embodiment of the present invention.

FIG. 5 is a flowchart 500 illustrating the process of identifying an unknown mineral sample according to an embodiment of the present invention. The first step 502 is to define each mineral. The mineral definition is typically established by analyzing many samples of a mineral and calculating a mean and variability measure for one or more mineral characteristics, such as the relative quantity of each element within the mineral. The value of the variability measure, such as a standard deviation of the relative elemental quantity measurement, is dependent in EDS on the number of photons collected: as the number of photons increases, the standard deviation typically decreases as there is less noise.

The mineral definition is therefore obtained using a relatively large number of x-rays, typically an order of magnitude or more x-ray counts than will be used to measure an unknown sample. For example, the definition may be determined using greater than ten times, greater than a hundred times, greater than a thousand, or greater than 10,000 times the sample of x-rays used to analyze an unknown sample. Preferably, mineral definitions are derived from multiple sample minerals measured at X-ray counts greater than 10,000 counts and more preferably at greater than 100,000 counts in order maximize accuracy. Furthermore, each particular mineral to be defined is preferably measured over 10 times, more preferably over 100 times, and most preferably over 1000 times. Definitions can be made to define all minerals that are currently known to exist. Definitions may also be derived from published standard data From the accurate "large count" standard deviation, an expected standard deviation can be calculated for a smaller number of counts using known statistical techniques, such as those for estimating the variation of a sample mean based from a population variation. This provides the system the ability to calculate, using the large count mineral definition, a modified mineral definition that is applicable to measurement performed at any number of x-ray counts. Thus, it is not necessary to measure each mineral at different numbers of x-rays counts to derive definitions useful at different number counts. In some embodiments of the invention, a mineral definition also includes other measured values, such as an average BSE intensity value, along with a variability measure for the values. The BSE intensity can therefore also be used in the calculation of an overall similarity metric to compare an unknown sample to the mineral definition.

Figure 6:
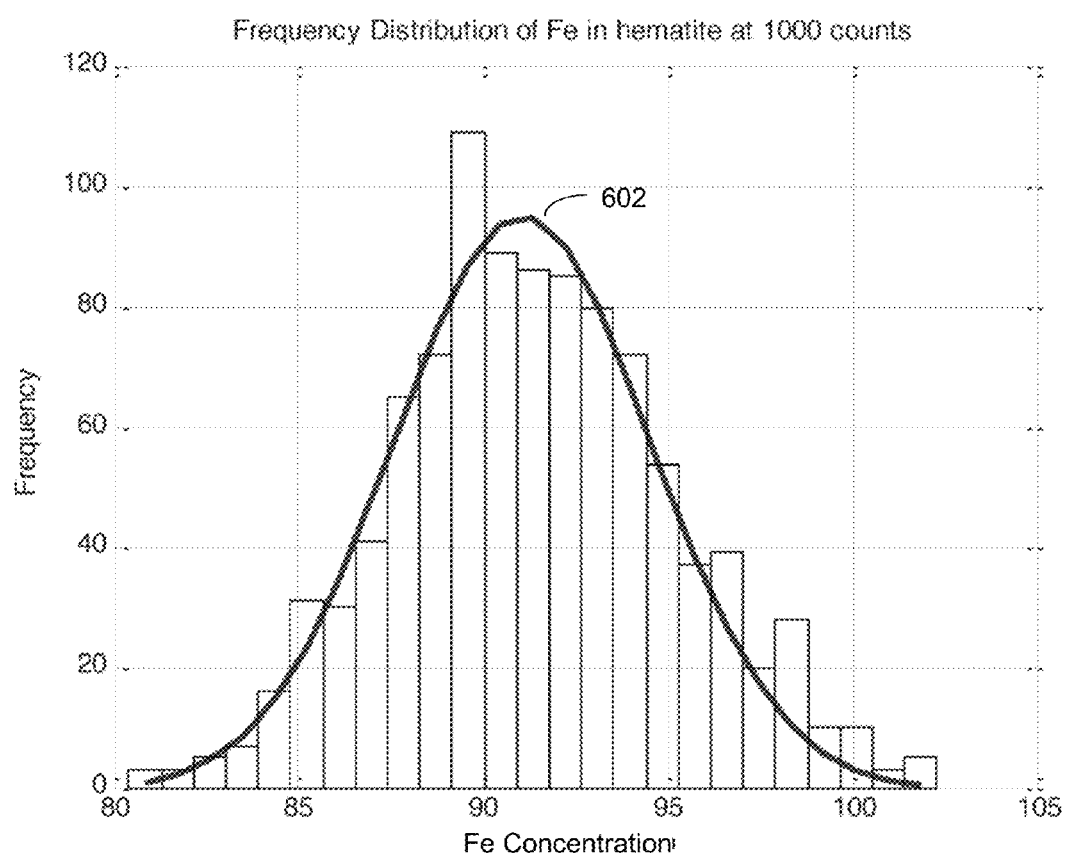
FIG. 6 shows an example histogram of the frequency distribution of the quantity of Fe in hematite at 1000 counts.

To illustrate the variability of a measured concentration, FIG. 6 shows an example histogram of the frequency distribution of the concentration of Fe found in hematite determined using spectra having 1000 counts. This distribution results in a Gaussian-like probability curve 602, which allows the determination of a mean and standard deviation using basic statistical analysis. Applicants note that the histogram in FIG. 6 does not need to be computed in order to calculate the mean and standard deviation for each element. Plotting a histogram is one way of computing these values, but persons of ordinary skill in the art will readily appreciate that other statistical means can be used as well. For example, the standard deviation at 1,000 counts, or other count values, can be calculated from the standard deviation determined from a high quality spectrum of 10,000 or 100,000 or more counts.

Figure 7:
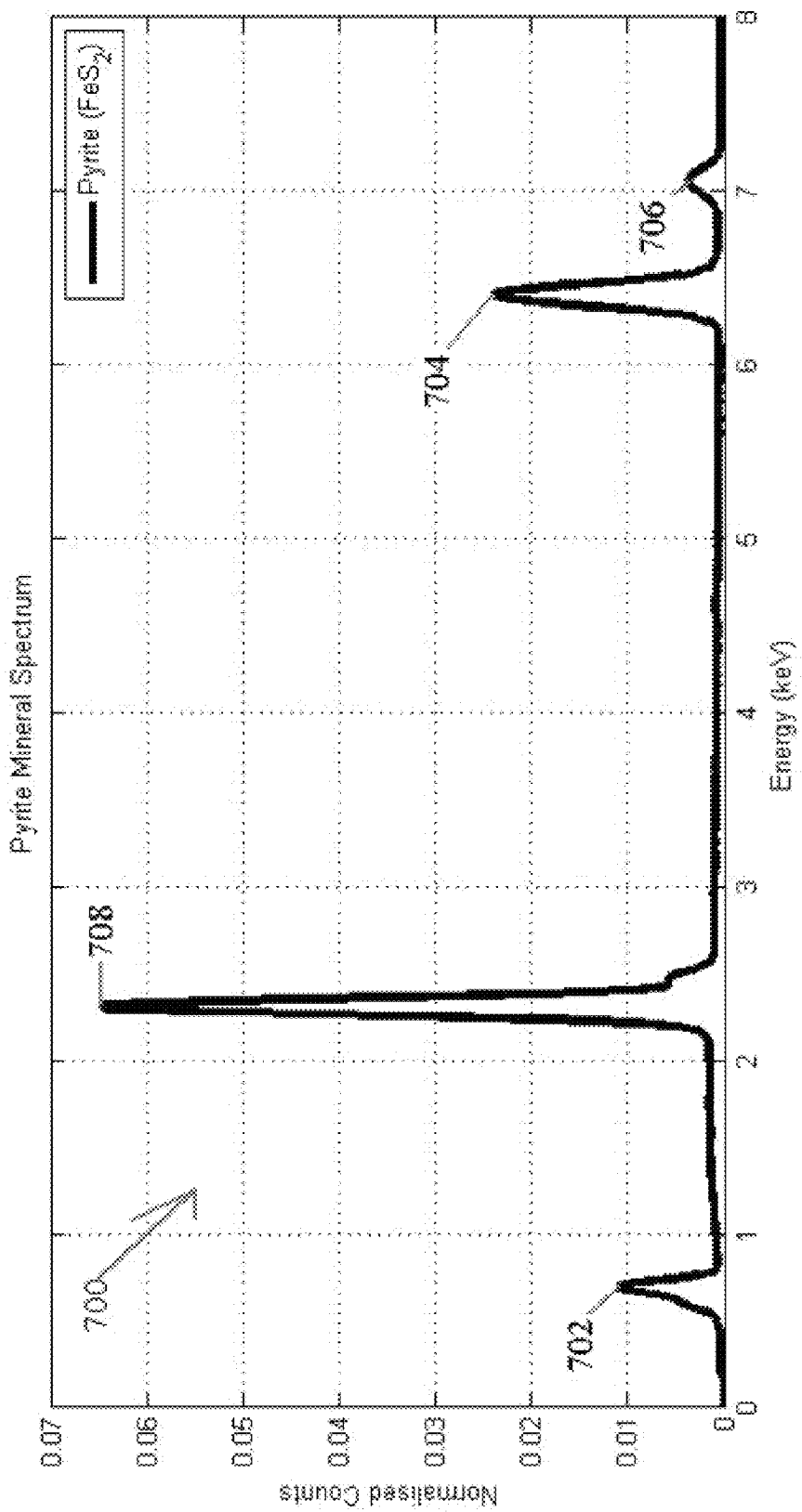
FIG. 7 shows a Pyrite spectrum measured using x-ray EDS.

Determining a mineral definition for pyrite. The mineral pyrite has a known chemical formula of $FeS_2$. FIG. 7 shows a Pyrite spectrum 700 measured using EDS. Peaks 702, 704, and 706 correspond to peaks for Fe at 0.7 keV, 6.25 keV, and 6.9 keV, respectively, and peak 708 corresponds to the peak from S at 2.28 keV. To create the mineral definition, a pyrite spectrum is measured, for example, 100 times at 100,000 counts each time, and a backscatter electron intensity value is recorded as well. The instrument is preferably calibrated such that the backscatter intensity for quartz is 44 and the backscatter intensity for gold is 227 on a scale of 0-255.

Figure 8:
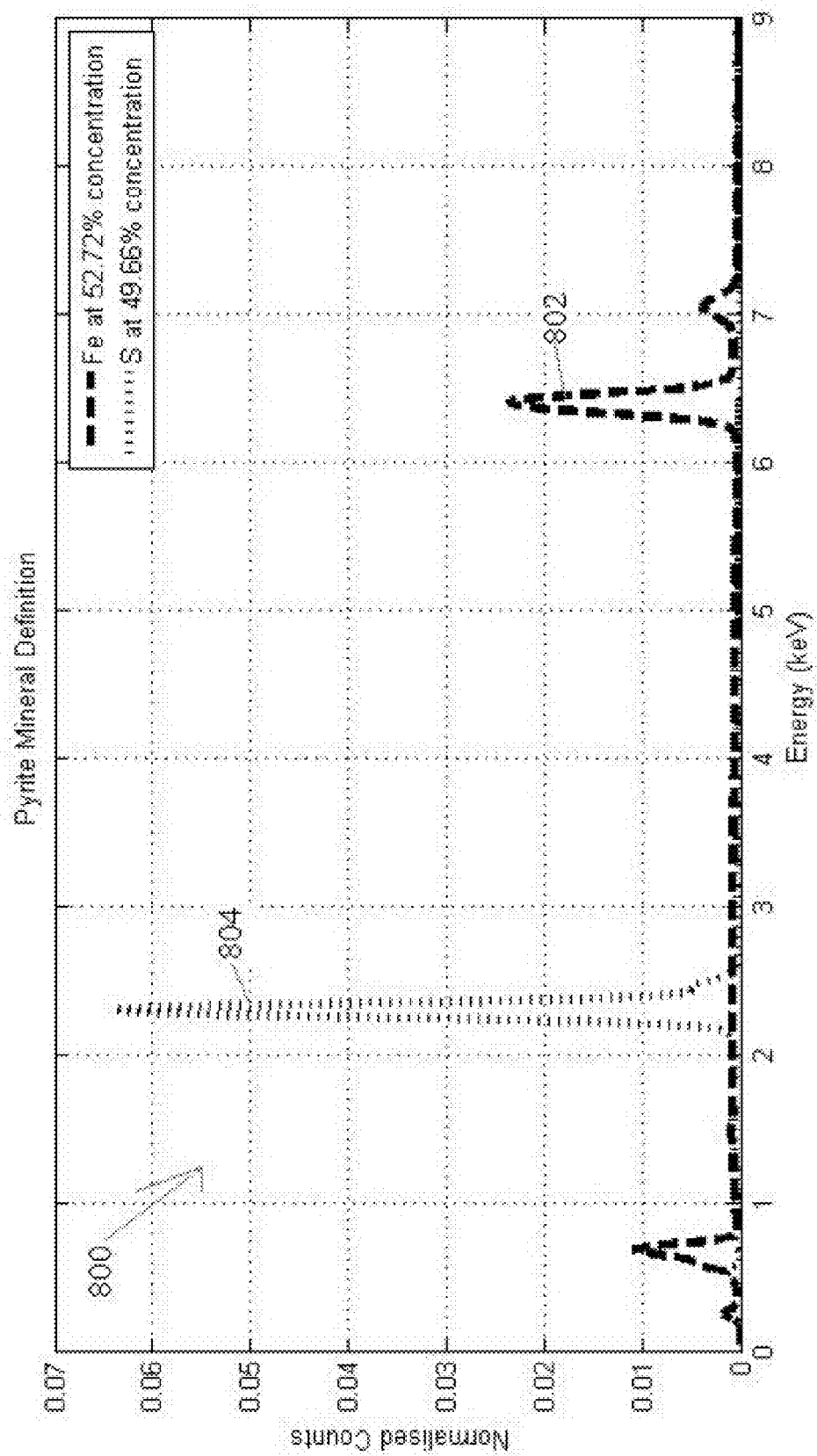
FIG. 8 shows an example of the best-fit curve for pyrite for the elements Fe and S in defining the mineral pyrite.

The known spectra of Fe and S are fitted to the curve 700 by varying the concentration of Fe and S until the best fit to the measured curve is obtained. FIG. 8 shows an example of the best-fit curve 800 for pyrite for the elements Fe (curve 802) and S (curve 804) in defining the mineral pyrite. If we repeat this curve fitting process 10,000 times for measured spectra of pyrite containing 100,000 photons in each spectrum, we obtain an average value for Fe=52.72% and S=49.66%, with a standard deviation for Fe=0.3124 and a standard deviation for S=0.2325. Plot 802 corresponds to S at 49.66% concentration and plot 804 corresponds to Fe at 52.72% concentration. The average BSE intensity was measured to be 91 with a standard deviation of 1.5.

The definition of Pyrite then comprises the values shown in the table below:

| Attribute | Mean Value | Standard Deviation |
|---|---|---|
| Fe | 52.72 | 0.3124 |
| S | 49.66 | 0.2325 |
| BSE | 91 | 1.5 |

The standard deviation at any lower count value ($\sigma_l$) is then predicted by the following model:

$$\sigma_l = \frac{\sigma_h}{\sqrt{\frac{l}{h}}}$$

Where l is the number of counts in the low count spectrum, h is the number of counts in the high count spectrum, and $\sigma_h$ is the standard deviation of the element concentration in the high count spectrum.

Thus, the standard deviation from the mineral definitions taken at high counts, for example at greater than 100,000 counts, can be used to predict the standard deviation when a user is measuring an unknown sample at lower counts, preferably less than 10,000 counts and more preferably less than 1,000 counts, thereby decreasing acquisition time while maintaining accuracy from the definition acquired at the high X-ray count.

After defining the minerals, step 504 includes storing these definitions in a database so that they can be easily accessed and used for comparisons with unknown mineral samples. Step 506 includes acquiring a spectrum of an unknown mineral sample. Step 508 then includes decomposing the unknown sample spectrum to determine the proportions of elements that are present in the unknown mineral. Fitting elemental spectra to the unknown sample spectrum can be accomplished by using well known methods to find solutions of over-constrained problems, such as the least squares method. In some embodiments, the unknown spectrum is decomposed into only the mineral in each mineral definition, sequentially. In other embodiments, the spectrum may be decomposed into all possible elements to determine which elements are present.

Figure 9:
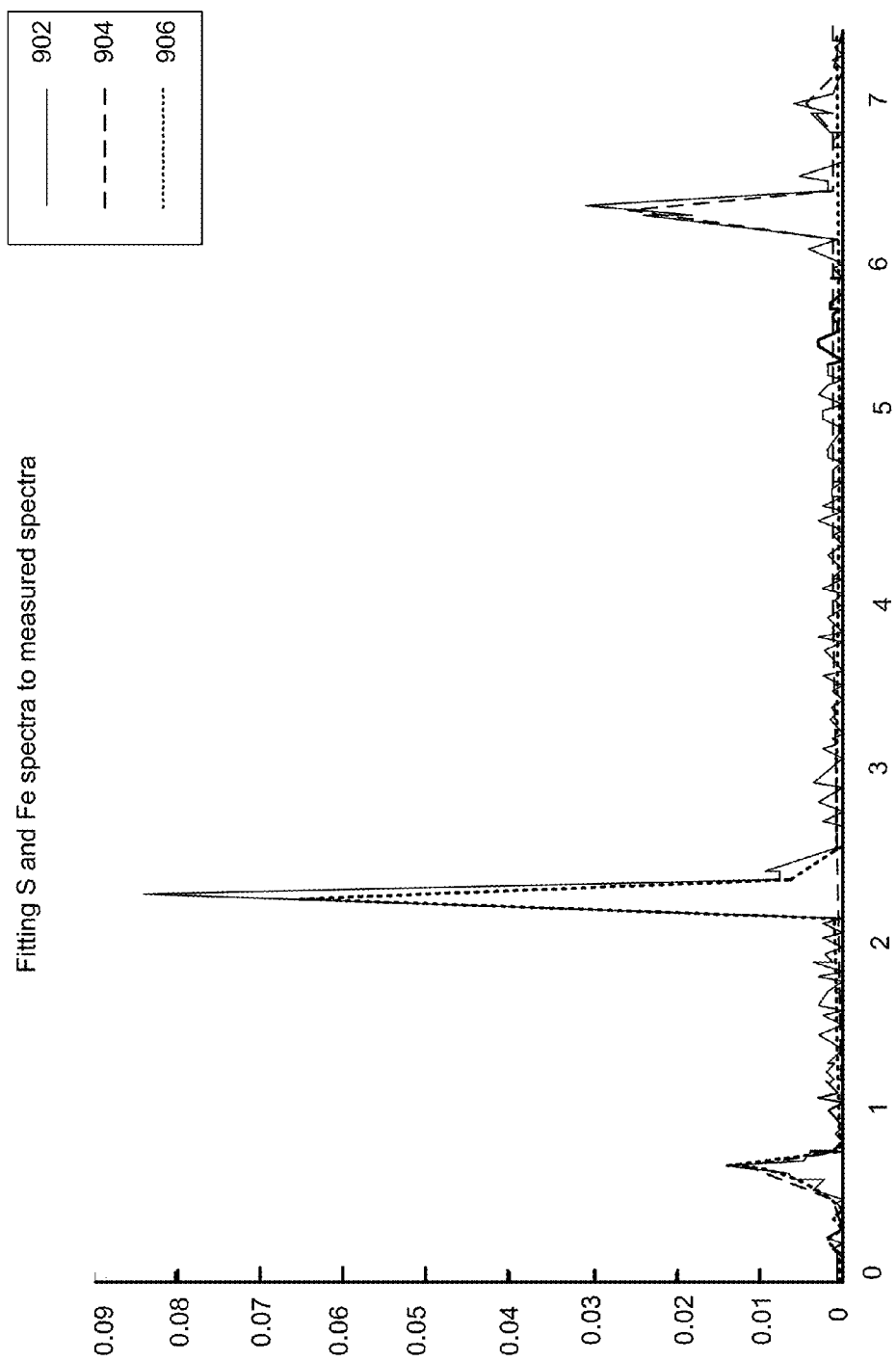
FIG. 9 shows an example of a curve-fitting spectrum for calculating the similarity of a measured spectrum to the mineral pyrite.

FIG. 9 shows an example of curve-fitting elements to a measured spectrum of an unknown mineral to calculate the similarity of a measured spectrum to the definition of the mineral pyrite. The elements of pyrite, sulfur (spectrum 904) and iron (spectrum 906), are fitted to the measured spectrum 902 to calculate the proportions of elements present. In this example, the curve-fitting analysis determined that the best fit was obtained assuming 49.52% sulfur and 53.07% iron.

Step 510 then calculates the probability that concentrations calculated for individual elements match the concentration of those elements in the mineral definition. For example, a definition of Pyrite, derived as described above by analyzing many samples of pyrite, was found to include S=49.66% and Fe=52.72%, with standard deviations of element of 0.2325 and 0.3124, respectively. Fitting the spectra of Fe and S to the curve in FIG. 9 finds proportions of 49.52% S and 53.07% Fe. In order to calculate a similarity metric to a mineral definition, a probability match for each individual element in the reference definition is first calculated using, for example, a Multivariate Normal Distribution model with the equations described below:

$z$=(Measured Value−Expected Value)/std_deviation

Probability (Element)=$erfc$(abs($z$)/sqrt(2))

where erfc is the complementary error function

| Element | Expected Value | STD Deviation | Measured Value | Z | P (Element) |
|---|---|---|---|---|---|
| S | 49.66% | 0.2325 | 49.52 | −0.6022 | 0.5471 |
| Fe | 52.72 | 0.3124 | 53.07 | 1.1204 | 0.2626 |

In this case, the individual probability matches for S and Fe are calculated to be 0.5471 and 0.2626, respectively. Computing the probabilities separately for each element, rather than computing only a single probability for the best fit curve, ensures that large peaks do not dominate the probability computation for the mineral. Step 512 then includes calculating the overall probability match to a mineral definition. The overall probability, for example, can be determined by using the product of the individual element probabilities.

$$P(\text{overall}) = P(S) * P(Fe)$$
$$= 0.5471 * 0.2626$$
$$= 0.1436$$

This final probability value is used as the similarity metric between the measured data and the mineral. Other similarity metrics, such as a distance metric, can also be used. Conditional step 514 then determines if there are any minerals left in the database to compare the unknown samples to. If there are more minerals, the process returns to step 510 which calculates the individual element probability match between the elements in the next mineral definition and then determines an overall probability in step 512. Once a comparison has been made between the unknown spectrum and all the mineral definitions in the database, the final step 516 includes selecting the mineral with the highest match probability. In some embodiments, if the probability fails to exceed a threshold, the mineral identification fails. The highest match probability value could be displayed to the user and/or a classification system could make use of this value to select the mineral which maximizes the similarity. The invention could also display the top matches, for example, the top 5 matches, for the user to review. Preferably, an embodiment of the invention displays the similarity metric calculated from the mineral identification process for the user to review.

Figure 10:
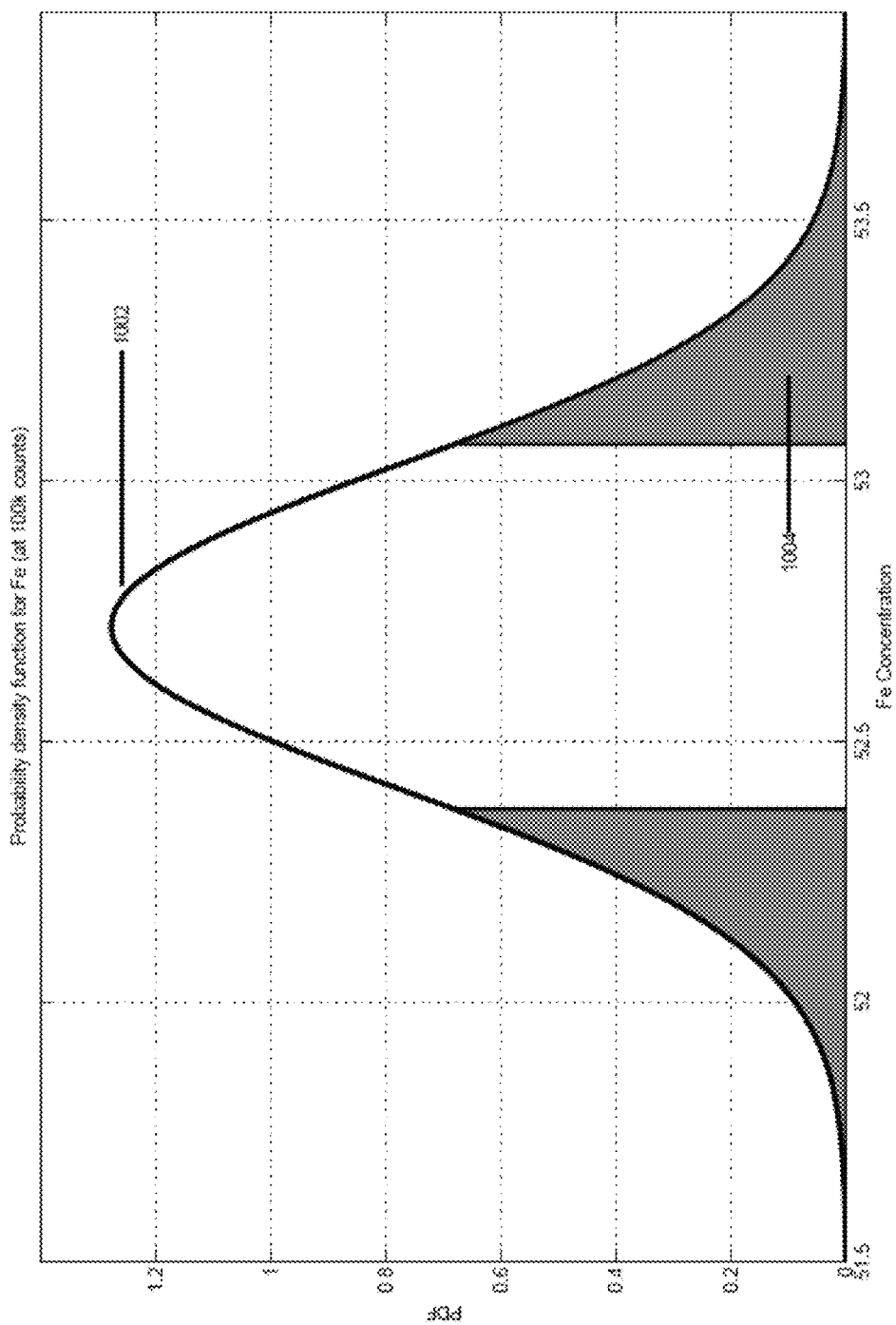
FIG. 10 shows a probability distribution for Fe and illustrates a way to calculate individual element probabilities.

FIG. 10 shows a probability distribution for the measured mean concentration of Fe. The shaded areas 1004 below curve 1002 represent the probability of all values further from the true concentration value, 52.72%, than the observed value of 53.07%. Integrating the shaded area 1004 from the observed value to positive infinity (and doubling it to account for the values at the same distance from the mean, but on the other side of the mean) provides the probability that the observed value of 53.07% will be measured when the true value of iron is 52.72%. Thus, from this combined shaded area, an individual element probability value can be computed. Consequently, an overall elemental probability can be computed by combining the individual elemental probabilities using a technique to combine independent probabilities, such as Fischer's method.

To better illustrate the mineral identification process, Applicants have provided the following example. An example database has three minerals that have been defined by analyzing multiple samples of each mineral to derive the following definitions:

| Mineral | Element | Expected Concentration | Standard Deviation at 100,000 Counts |
|---|---|---|---|
| Quartz | Si | 85.2697 | 0.2335 |
|  | O | 14.7362 | 0.1568 |
| Pyrite | Fe | 52.72 | 0.3124 |
|  | S | 49.66 | 0.2325 |
| Chalcopyrite | Cu | 19.6662 | 0.2248 |
|  | Fe | 44.8094 | 0.2986 |
|  | S | 35.5361 | 0.2151 |

An unknown spectrum is first measured with 1000 counts. The elements for Quartz (Si, O) are fitted onto the spectrum giving concentrations of: Si=83.83 and O=13.34. Then the standard deviation for a 1000 count spectrum is calculated by using the formula: $stddev_{1000} = stddev_{100000}/\sqrt{100/1000000}$. The individual probabilities for Si and O in Quartz are calculated, and the joint probability is finally calculated. These calculations are repeated for each mineral definition in the database, and the calculations are summarized in the table below:

| Mineral | Element | Measured Concentration | Expected Concentration | Standard Deviation at 100,000 Counts | Standard Deviation at 1000 counts | Measured Element Probability | Joint Probability |
|---|---|---|---|---|---|---|---|
| Quartz | Si | 83.83 | 85.2697 | 0.2335 | 2.335 | 0.5375 | 0.20 |
|  | O | 13.34 | 14.7362 | 0.1568 | 1.568 | 0.1265 |  |
| Pyrite | Fe | 11.05 | 52.72 | 0.3124 | 3.124 | ~1.4e−40 | ~2.5e−128 |
|  | S | 3.30 | 49.66 | 0.2325 | 2.325 | ~1.8e−88 |  |
| Chalcopyrite | Cu | 8.11 | 19.6662 | 0.2248 | 2.248 | ~2.7e−7 | ~6.9e−88 |
|  | Fe | 10.36 | 44.8094 | 0.2986 | 2.986 | ~8.6e−31 |  |
|  | S | 3.14 | 35.5361 | 0.2151 | 2.151 | ~2.9e−51 |  |

From the calculations from the table above, it can be determined that the Quartz definition maximizes the joint probability compared to the other mineral definitions. Thus, and embodiment of the present invention calculates and outputs this similarity metric between the unknown sample and the mineral definitions. The similarity metric can be displayed using, for example, a monitor attached to the apparatus in FIG. 2.

The preferred probability calculation makes the assumption that all elements in a mineral vary independently. This allows for efficient computation of the probabilities for the elements. Applicants have found that the accuracy of the calculation can be considerably improved by considering the covariance between elements in the mineral. For example, in Pyrite defined as Fe=52.72% S=49.66%, when Fe is detected at more than 52.72%, the expected concentration of S would be less than 49.66%. The covariance can be calculated by measuring many examples of a mineral and applying the following formula:

$$Q_{ij} = \frac{1}{N} \sum_{k=1 \ldots N} (C_{ik} - \overline{C_i})(C_{jk} - \overline{C_j})$$

Where:
N is the number of mineral example calculations;
$Q_{ij}$ is covariance between elements with atomic numbers i and j in the mineral;
$C_{ik}$ is the concentration of element with atomic number i, in the $k^{th}$ example of the mineral;
$\overline{C_i}$ is the average concentration of element with atomic number i in all N examples of the mineral;
$C_{jk}$ is the concentration of element with atomic number j, in the $k^{th}$ example of the mineral;
$\overline{C_j}$ is the average concentration of element with atomic number j in all N examples of the mineral.

Once the covariance matrix is calculated, the probability of obtaining element concentrations is computed using a multivariate normal cumulative distribution function that is well known. Furthermore, a function such as MATLAB's COV could be used to calculate the covariance matrix from known mineral samples and a function such as MATLAB's MVNCDF can be used to calculate the overall probability given the expected element values, measured element values, and covariance matrix.

This calculation of a similarity metric can be extended to include information from other detectors, such as BSE detectors. The BSE signal is only a single value representing the average atomic number at a point in the sample, so curve fitting is not required. The mineral definition would contain an expected value for BSE and a calculated standard deviation from multiple known samples.

The unknown mineral sample is identified with the mineral definition having the best similarity metric, that is, the highest probability of matching, and optionally, that exceeds a predetermined threshold value. In other embodiments, the mineral definition is used to determine matching rules whose ranges have widths that reflect the number of x-ray counts used to measure the unknown spectrum. The width of the ranges can be determined based on a predetermined probability value, and can be used in a first match system.

Elemental Quantification

Figure 11:
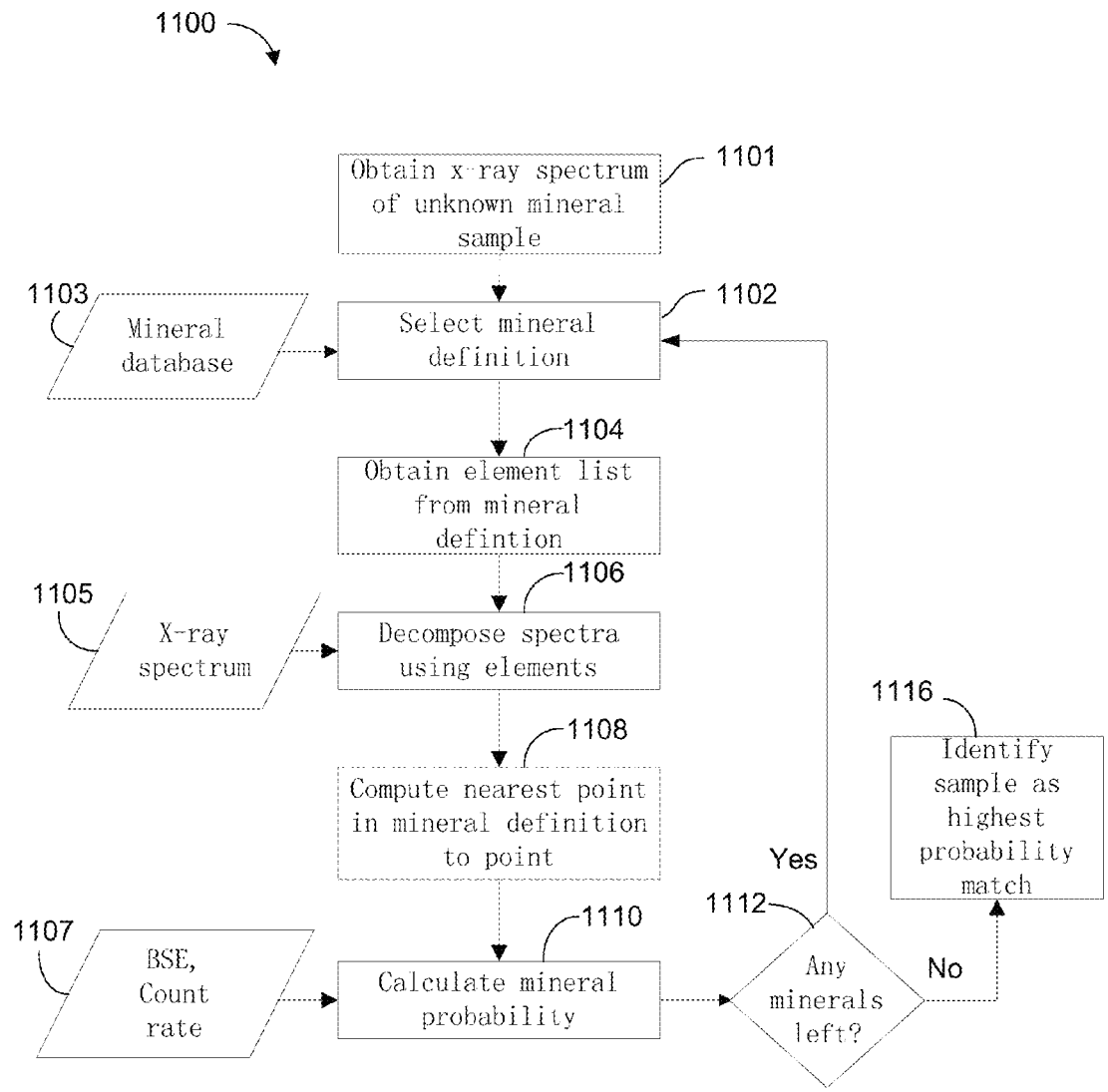
FIG. 11 shows a flowchart illustrating the steps for elemental quantification and calculating a mineral probability from this quantification.

FIG. 11 shows a flowchart 1100 illustrating the steps for elemental quantification and calculating a mineral probability from this quantification according to an embodiment of the present invention. In prior art systems such as the QEMSCAN, mineral definitions may state that the mineral may contain Na or may contain Zn. This embodiment preferably does not require tracking multiple elemental possibilities when determining mineral content. In a preferred embodiment, a mineral is preferably defined with a fixed set of elements and each element has a value that represents the concentration of the element in that mineral. This set of elements may be the full set of 92 elements in some embodiments, or may be a sub-set of these in other embodiments. Limiting the number of elements in the mineral definition is useful when quantifying a spectrum when the mineral is known. In some applications, the mineral definition specifies the full set of 92 elements for identifying the mineral, but can specify a sub-set of these for elemental quantification. As the mineral definition specifies the element set, the mineral matching algorithm takes the element set and calculates the mineral probabilities. This embodiment may be used together with the previously described embodiment, in which the mineral definitions also include a measure of variability of the measured parameters, which facilitates matching of the unknown mineral with the mineral definitions. This embodiment can also be used with mineral definitions that do not include variability. Some embodiments include decomposing the spectrum of the unknown mineral into the elements from each of the mineral definitions, in turn. The mineral definition that produces the best match, above a threshold, is used to identify the mineral.

In step 1101, an x-ray spectrum is obtained from an unknown mineral sample. The x-ray spectrum preferably includes a relatively small number of x-ray counts, such as less than 10,000 counts, less than 5,000 counts, or less than 2,000 counts, and preferably about 1,000 counts, to reduce measurement time. A first mineral definition is selected in step 1102 from the database 1103 of mineral definitions. Step 1104 then includes obtaining a set of elements, or an element list, from the selected mineral definition. Step 1106 entails decomposing the acquired spectra 1105 using the element list form the selected mineral definition. That is, assuming that the sample of unknown composition is composed of the elements in the element list of the material definition, step 1106 comprises determining the relative amounts of the elements from the mineral list in the spectrum acquired from the sample. For each mineral in the database, this embodiment selects a set of elements for quantification that are defined for just that mineral. For example, if the mineral definition was Nickel Silicide ($Ni_2Si$) then an element list could include nickel and silicon, and the spectrum would be decomposed solely in terms of Ni and Si, regardless of whether or not they are actually present in the x-ray spectrum. Some mineral definitions may include all 92 elements, to force the system to determine a relative quantity of all elements. The elements used in the decomposition are determined by the mineral definition in the database. By choosing an element set directly from a database with mineral definitions, applicants have discovered that the quantification of elements can be done very accurately.

Decomposing the X-ray spectra of the unknown mineral using the element list in step 1106 can be done in a variety of ways. In some embodiments of the invention, the energy range of the spectrum is divided into windows and an element is assigned to try to match each window. In some embodiments, the unknown spectrum is decomposed against elemental x-ray standards. The elemental spectra for the mineral definition is first split into segments, each segment based on a peak present in the unknown mineral spectrum. EDS equipment providers have published element line energy tables, such as the EDAX Peak Identification Chart, documenting the energies at which each element will emit x-ray photons. The element segments are defined as the regions of the element spectrum around known peak energies, for example, from the EDAX Peak Identification Chart. The width of each elemental segment is preferably defined as the range: E−FWHM, E+FWHM. Where FWHM is given by the formula:

$$FWHM = \sqrt{R^2 + 2.4236(E - 5894)}$$

E=element peak energy; R=EDS detector resolution at MnKα. FIGS. 12 and 13, explained in more detail below, further illustrate the benefits of splitting the x-ray spectra into elemental segments.

The next step in decomposing the X-ray spectra is to fit elemental x-ray spectra segments of the mineral definition against the x-ray spectrum of the unknown material. This curve-fitting will lead to a calculation of coefficients for each element from the element list that was selected. Using a linear least squares approach, the following equation would be created and solved: S=Ax; where: S is a vector of the counts in the spectrum for the unknown mineral being decomposed, A is a matrix of elemental spectra being used for decomposition, x is the coefficient representing the concentration of each element as calculated from the contributions in the x-ray spectra. Alternatively, decomposing the X-ray spectra could include performing curve-fitting without first splitting the spectra into segments. If the curve fitting includes some kind of linear decomposition, such as minimizing the least squares or least absolute deviation, the x-ray spectrum for the elemental standards can first be split into segments to account for non-linearity in the x-ray response of the elements.

Figure 19:
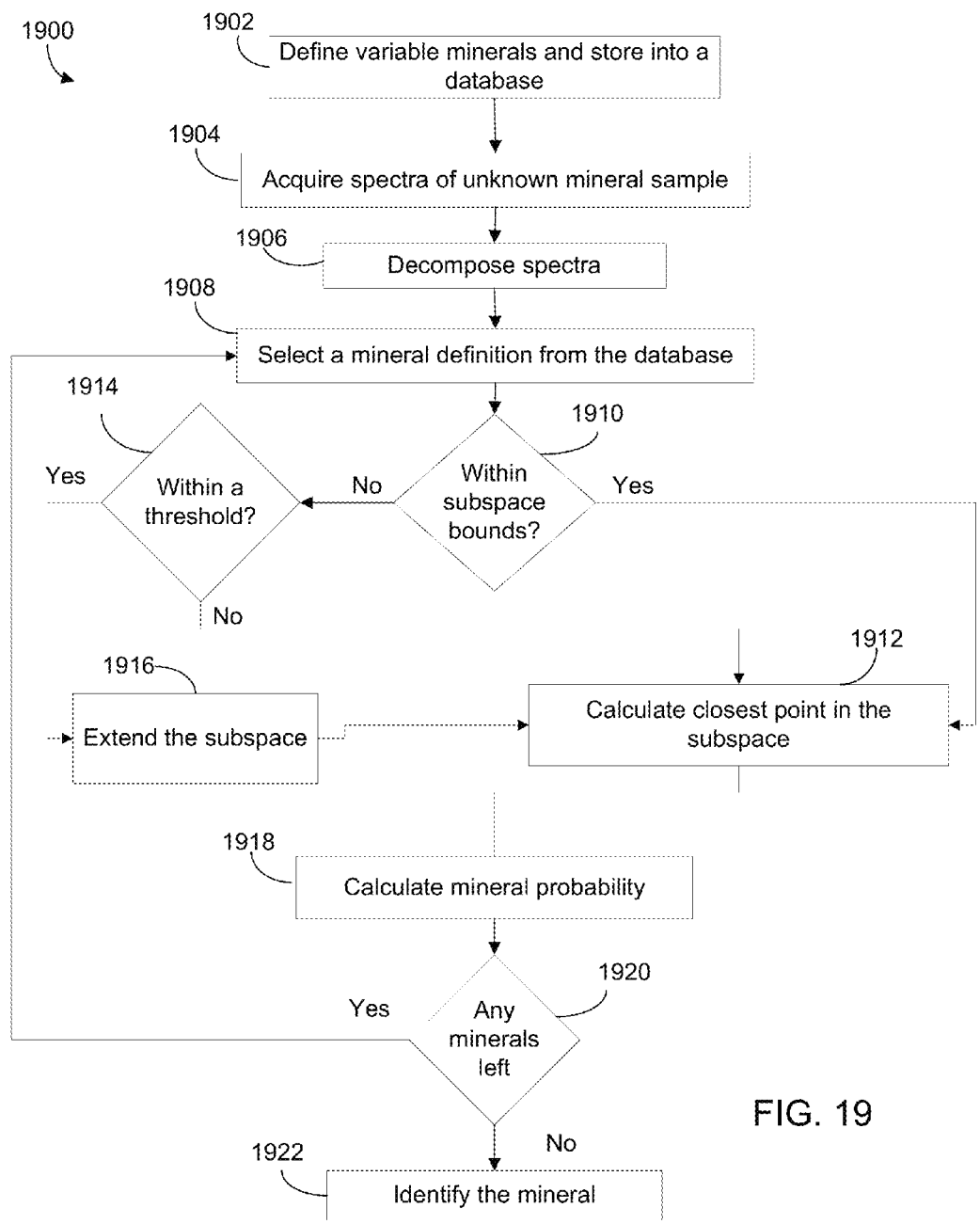
FIG. 19 is a flowchart showing the steps of a mineral analysis in which the elements at least one of the minerals has an allowed range of values.

If the mineral definition includes a range for the relative amount of an element, rather than a single value, optional step 1108 computes the nearest point in the mineral definition to the values from the decomposed spectra. This is explained in more detail below. This can be accomplished through known statistical methods, for example, by using the least squares method to find the distance between the measured spectra point and the closest point in the mineral definition. FIG. 19 describes in detail how to select the closest point in a mineral definition for variable compositional minerals.

Step 1110 then calculates the mineral probability as described above, by first calculating match probabilities for individual elements and then combining the individual elemental probabilities to form an overall probability that the composition of the sample matches the mineral from the database. When the mineral definition includes all 92 elements to force decomposition into all 92 elements, the mineral definition would include a zero relative quantity for elements that are not part of the mineral during the matching process. Other information that can be used for matching, such as information from the x-ray count rate and/or a BSE intensity value, is represented by block 1107, and is optionally incorporated in the calculation of the mineral probability. Like the element concentrations, the BSE value for a known mineral can be measured multiple times such that a mean and standard deviation can be calculated. An individual probability of a match for BSE other data is calculated using the mean and standard deviation, then this probability is included in the multiplication of all elemental probabilities to give the final joint probability. The x-ray count, the number of x-ray photons emitted per second of acquisition time, can also be included in the mineral definition and measured in the unknown sample as another value to be used in the matching. A probability for an individual element can be calculated from a mean and standard deviation for count rate, and included in the multiplication for the overall probability.

The process of determining a similarity metric or probability of a match between each mineral definition and the unknown mineral is continued until all mineral definitions have been tested. Condition statement 1112 determines whether or not all mineral definitions have been tested. If some mineral definitions have not been tested, the process of determining the probability of a match is repeated from step 1102 with the next mineral in the database. If more than one mineral definition include the same set of elements, it is not necessary to repeat the decomposition into the same set of elements multiple times. For example, if a mineral definition indicates that the decomposition should be into all 92 elements, than the results of that decomposition can be used for every mineral definition that uses 92 elements. If all minerals in the database have been tested, step 1116 will identify the unknown mineral as the mineral definition with the best similarity metric, such as the highest probability match. The mineral definition having the best match can also be displayed, along with the actual probability value or other similarity metric that was calculated. In some embodiments, the process may be stopped before all the mineral definitions are tested, if a tested mineral definition corresponds to a high enough probability of a match.

Figure 12A:
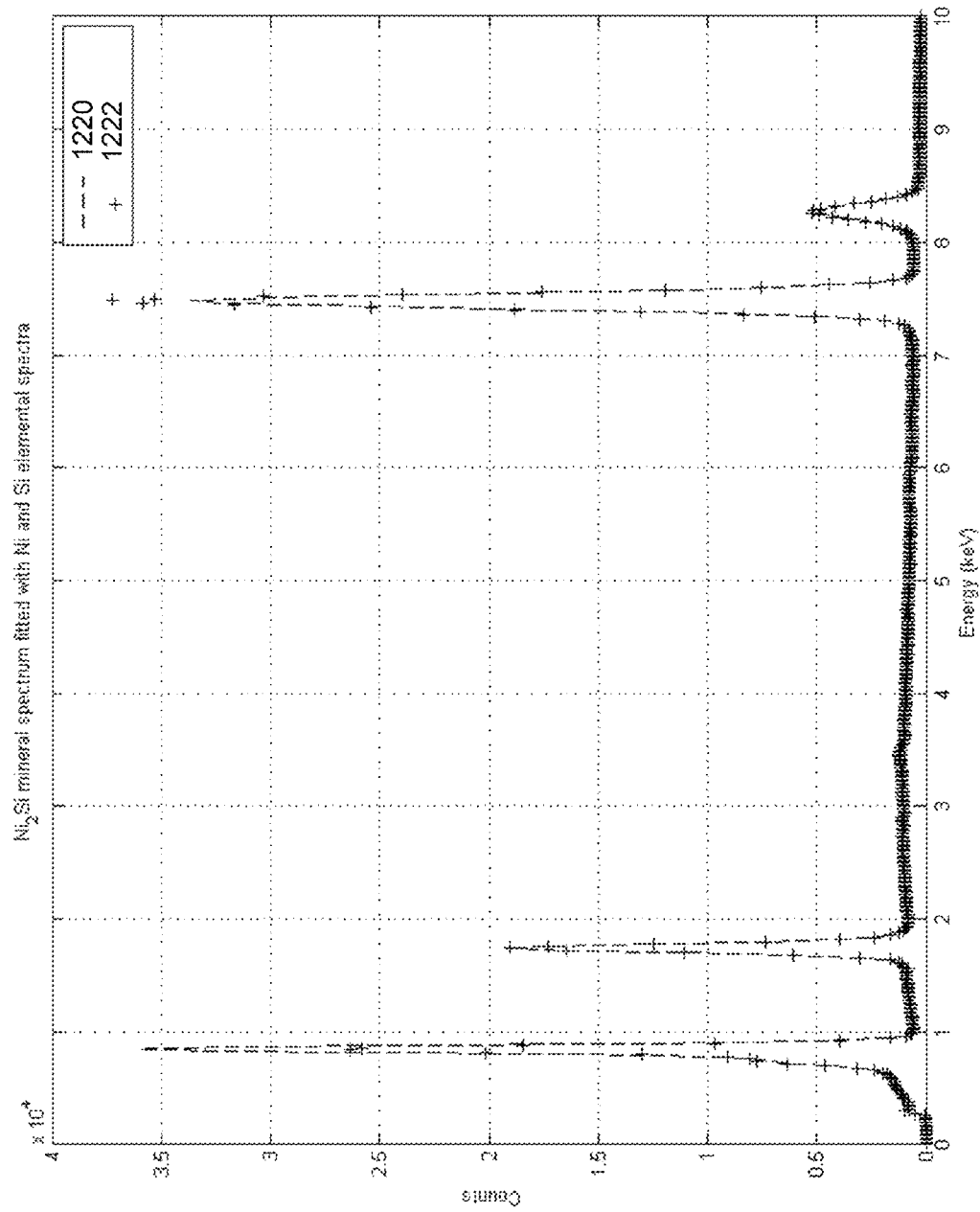
FIGS. 12A-12C illustrate the method of curve fitting elemental standards to measured spectra without splitting the elemental spectra into segments based on the number of peaks present in the spectra.
Figure 12B:
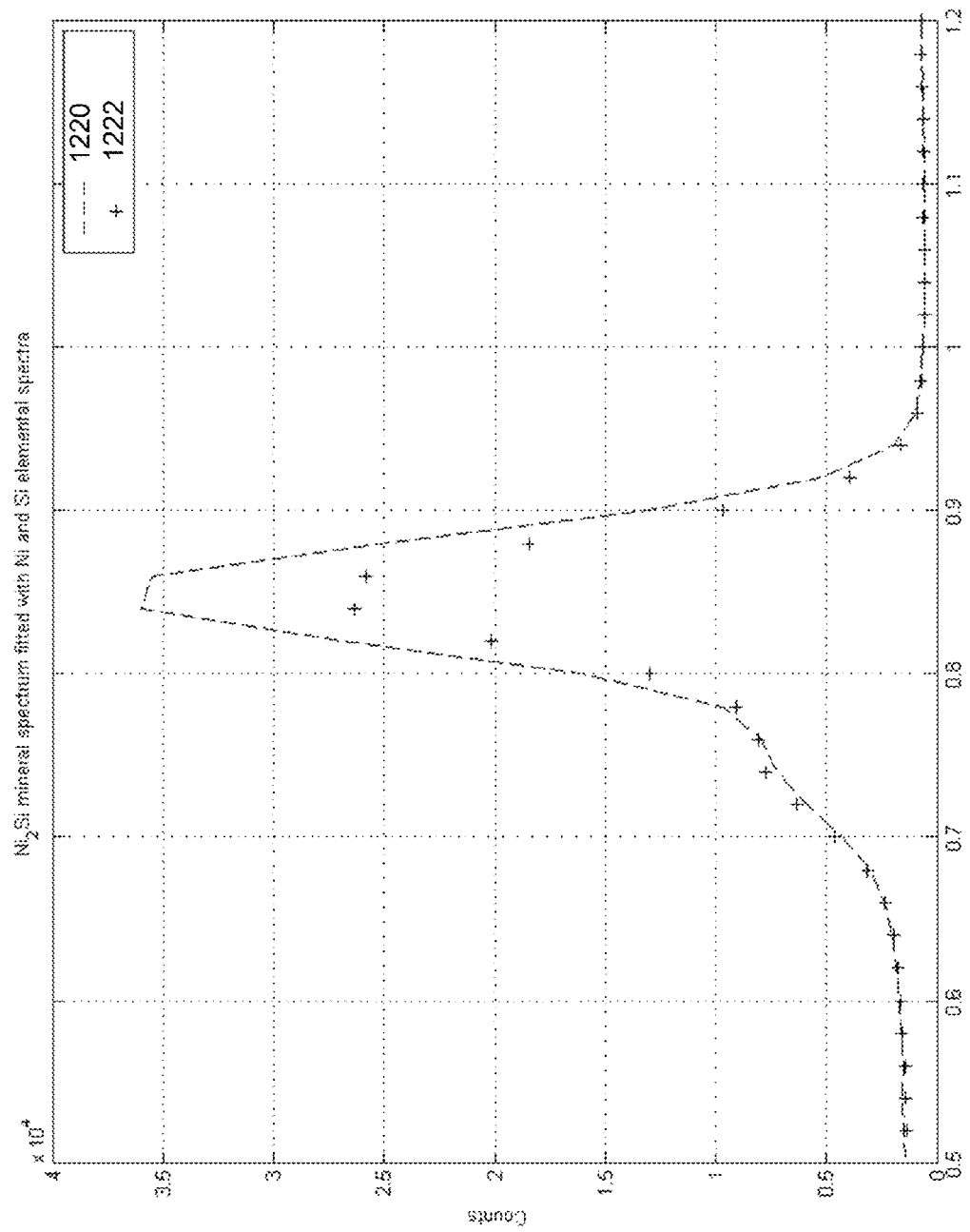
Figure 12C:
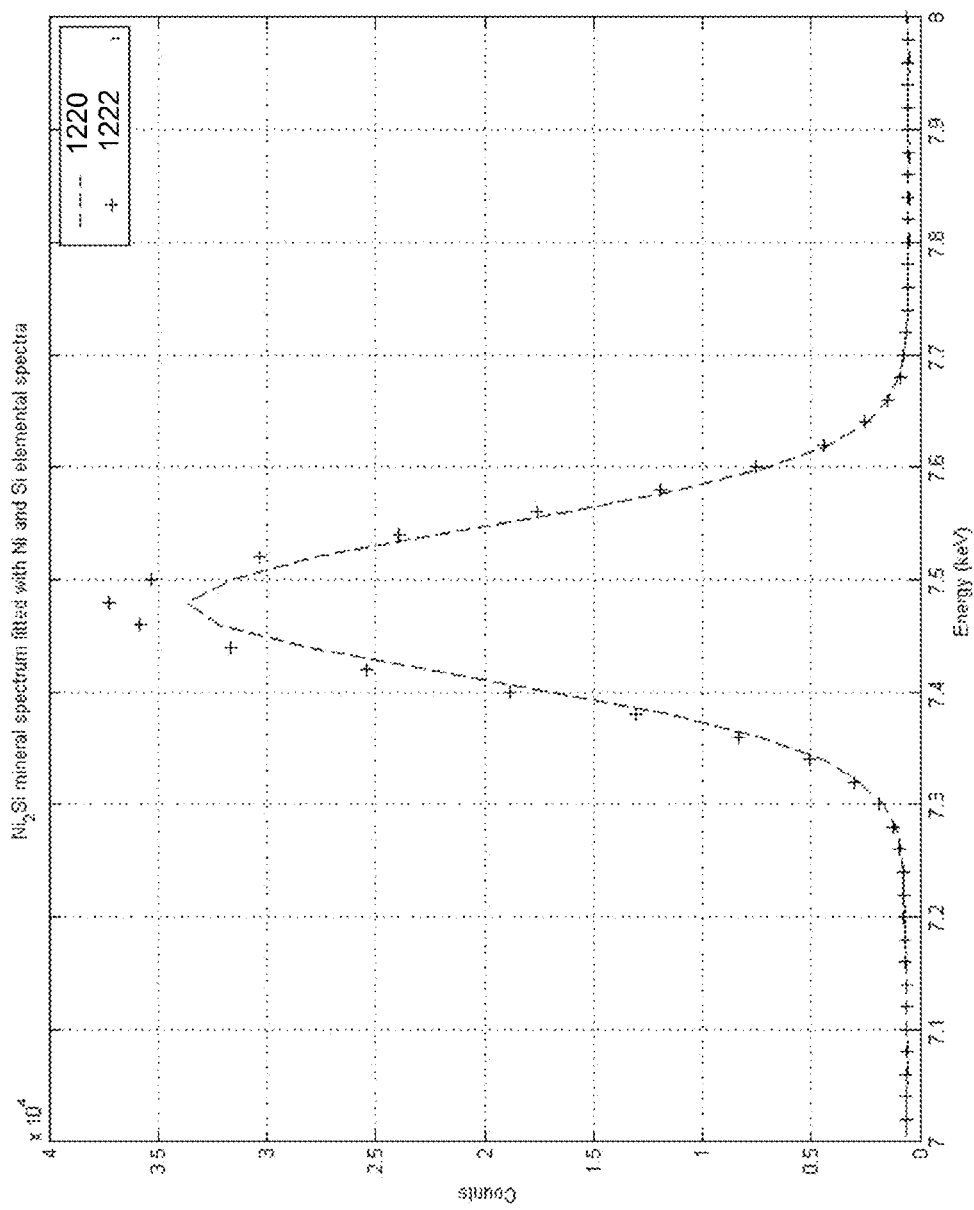
Figure 13A:
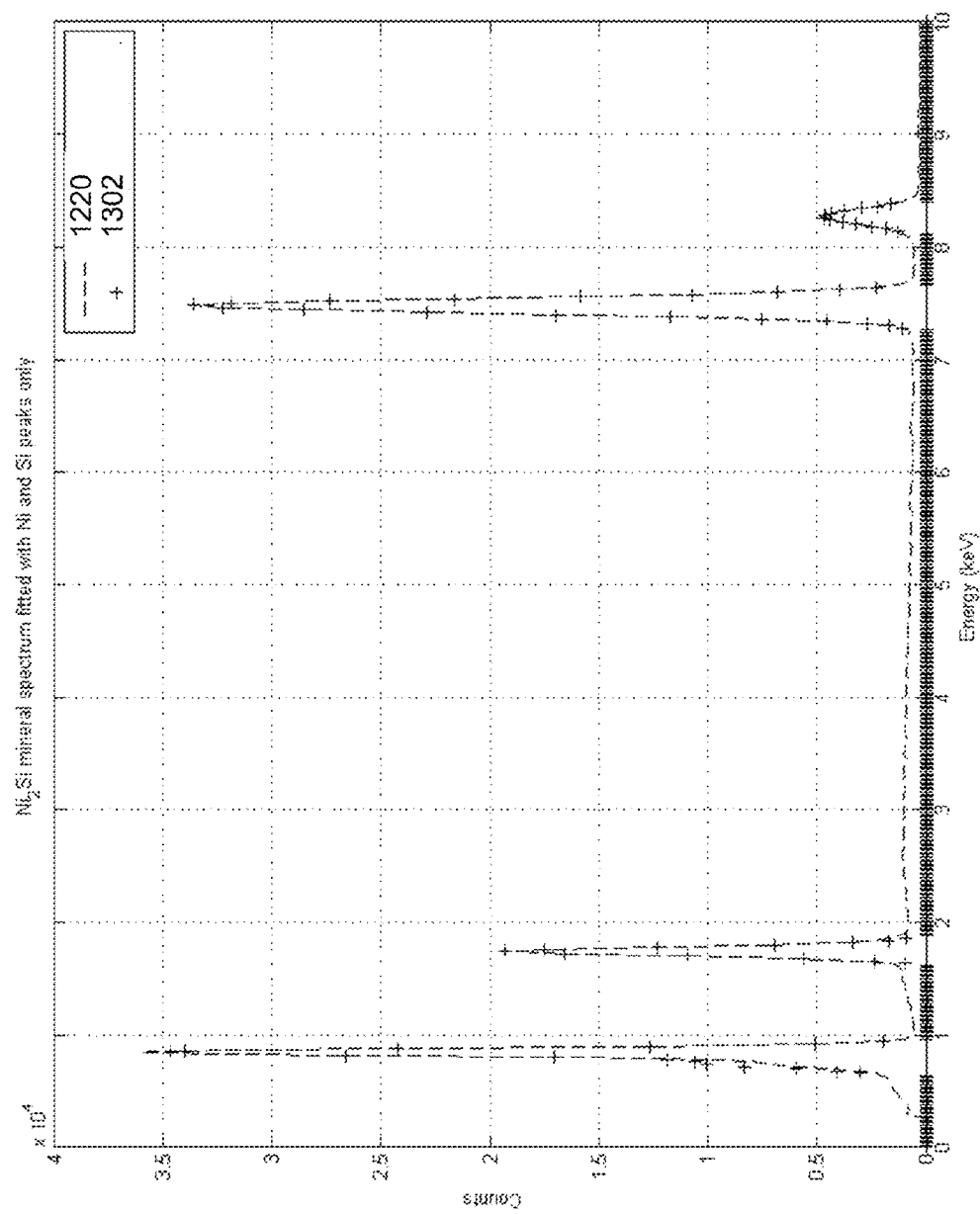
FIGS. 13A-13C illustrate the advantages of splitting the elemental standards into segments before fitting the elemental standards spectra to the measured spectra.
Figure 13B:
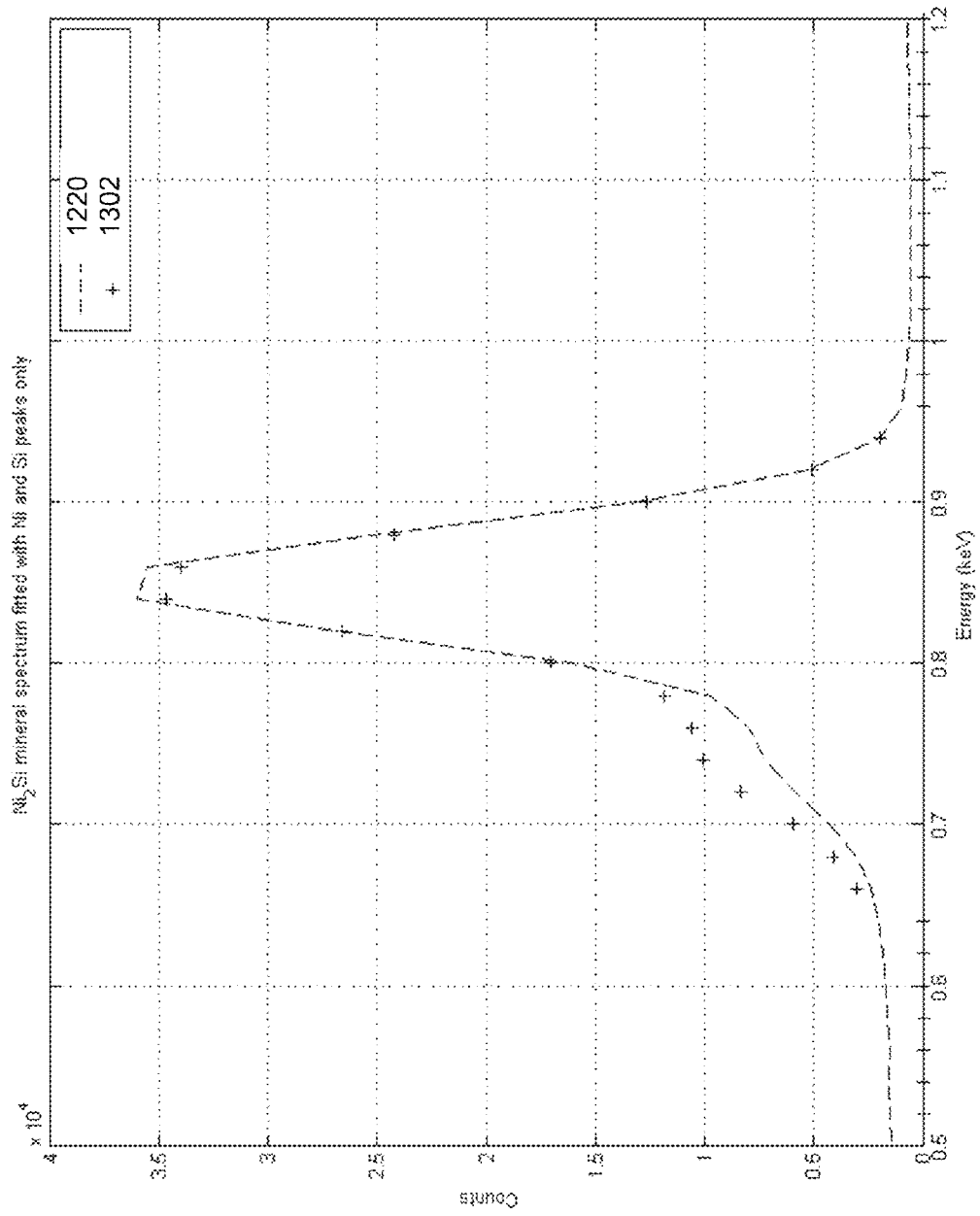
Figure 13C:
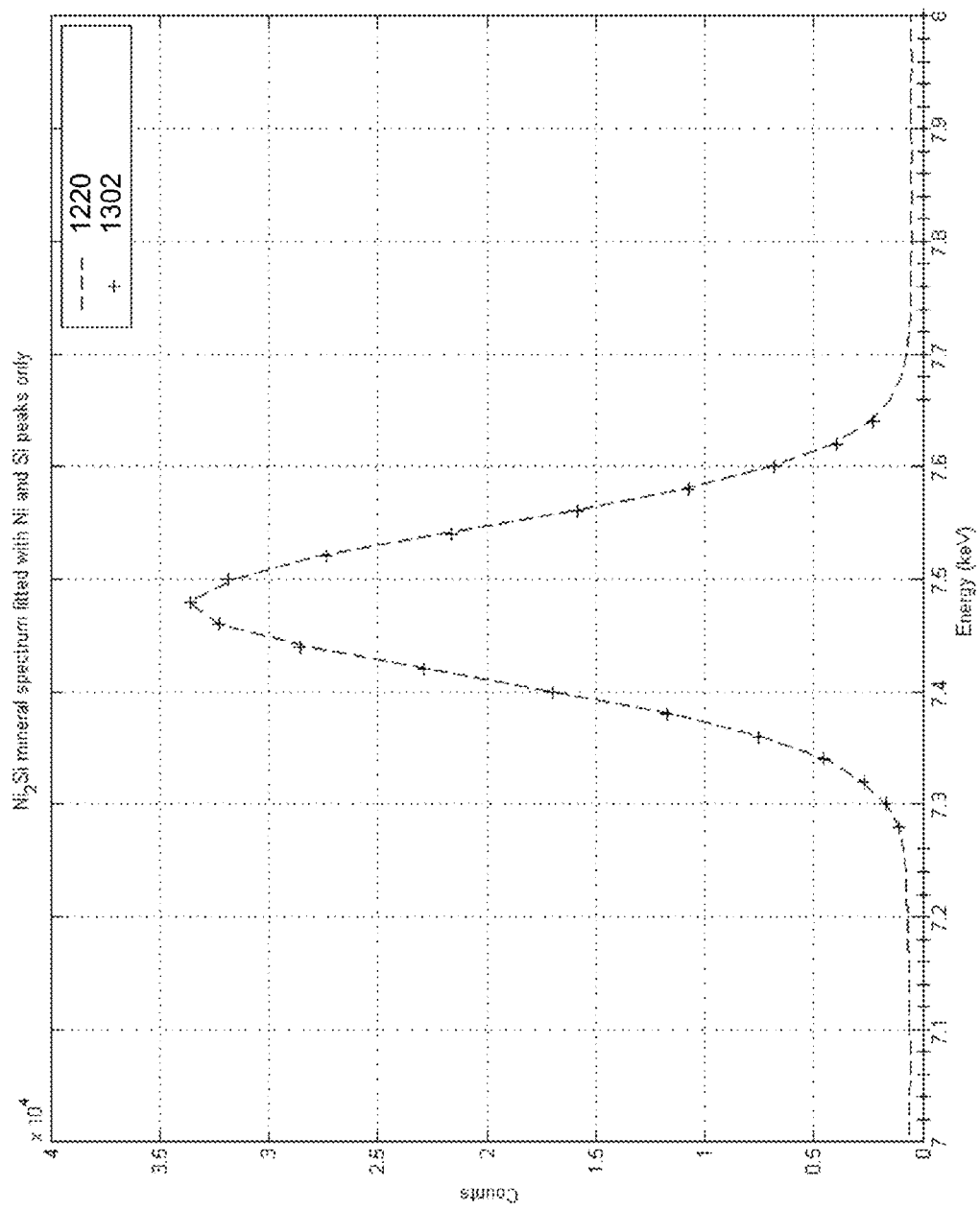

FIGS. 12A-12C and 13A-13C illustrate curve-fitting techniques than can be used in step 1106 of FIG. 11. FIGS. 12A-12C illustrate the method of curve fitting elemental standards to measured spectra without splitting the elemental spectra into segments based on the number of peaks present in the spectra. FIGS. 13A-13C illustrate an embodiment of the invention in which the elemental standards are split into segments before fitting the elemental standards spectra to the measured spectra.

FIG. 12A shows a graph of $Ni_2Si$ spectra acquired from the sample fit against the standard spectra of Ni and Si without splitting the Ni or Si spectra into separate segments. This fitted graph is obtained by using a linear curve fitting method, for example, using linear least squares. Plot 1220 represents the $Ni_2Si$ sample spectrum, while plot 1222 represents the fitted spectrum of the elemental standards Ni and Si. FIG. 12B shows an enlarged portion of the graph of FIG. 12A around the Ni peak at around 0.85 keV. FIG. 12B shows that the fitted spectrum 1222 is too small for the Ni peak at 0.85 keV. FIG. 12C also illustrates how fitted spectrum 1222 is too high at the higher Ni peak at 7.5 keV. This indicates that the coefficient calculated for Ni has been skewed by the change in the relative peak heights in $Ni_2Si$. Thus, without splitting the elemental standards into segments, the fitted curve may result in mineral misidentification.

FIGS. 13A-13C illustrate the advantages of splitting the elemental standards into segments before fitting the elemental standards spectra to the measured spectra. Each segment of the elemental standard preferably corresponds to a peak and each segment is then separately fitted to the corresponding segment, that is, the energy range corresponding to that of the segment, of the unknown spectrum. For example, the scaling factor or other coefficients used to match the segments may be different for matching different segments of the spectrum. FIG. 13A illustrates a $Ni_2Si$ spectra fit against the peak segments of Ni and Si. Each segment is fitted independently of other peaks, and fitted spectrum 1302 now matches the $Ni_2Si$ spectrum 1220 more closely. In addition, the splitting of elemental standards also helps avoid fitting the shape of the background Bremsstrahlung region, which is not characteristic of any element. FIGS. 13B and 13C, which show zoomed in portions of FIG. 13A shows that the fitted spectrum 1302 more closely matches spectrum 1220 at peaks at 0.85 keV and 7.5 keV, respectively.

Applicants have found that by choosing an element set directly from the mineral definitions, the quantification of elements can be performed very accurately, particularly when using segment-by-segment curve fitting. QEMSCAN's existing elemental identification and quantification may have difficulty selecting the most likely set of elements for quantification. In contrast to the QEMSCAN method, where all elements may possibly exist in a measured spectrum, the present approach assumes that only those elements listed in the mineral definition are present in the spectrum when calculating probabilities. Moreover, since the elemental percentages are calculated using all elements from the mineral list, without first identifying which elements may be in the unknown sample, the lower detection limits for elements is decreased. In some preliminary testing of the mineral jadeite, the concentration of Fe was 0.72% and the concentration of Ca was 1.23%. When these were analyzed using the standard QEMSCAN® elemental quantification algorithm, the detection rates, that is, the percentage of time that these elements were detected in the mineral sample, are shown below. In all cases, the method described above provides higher detection rates for low concentration elements when using low-count x-ray spectra. This means that the algorithm reports that the element has been detected in the x-ray spectrum. The tables below show the differences in detection rate between the prior art QEMSCAN and the embodiment described above.

TABLE 1

Calcium Detection Rates (concentration 1.23%)

| X-ray Counts | Detection Rate (QEMSCAN) | Detection Rate (New Embodiment) |
| --- | --- | --- |
| 100 | 70.7% | 89.9% |
| 250 | 89.4% | 98.5% |
| 500 | 97.8% | 100% |
| 750 | 99.4% | 100% |
| 1000 | 99.9% | 100% |
| 2000 | 100% | 100% |

TABLE 2

Iron Detection Rates (concentration 0.72%)

| X-ray Counts | Detection Rate | Detection Rate (New Embodiment) |
|---|---|---|
| 100 | 58.5% | 74.8% |
| 250 | 80.4% | 94.3% |
| 500 | 95.5% | 99.1% |
| 750 | 98.7% | 100% |
| 1000 | 99.8% | 100% |
| 2000 | 100% | 100% |

TABLE 3

Magnesium detection rates (concentration 0.43%)

| X-ray Counts | Detection Rate | Detection Rate (Proposed) |
|---|---|---|
| 100 | 51.7% | 75.8% |
| 250 | 65.5% | 85.2% |
| 500 | 79.5% | 95.8% |
| 750 | 86% | 97.9% |
| 1000 | 92.8% | 99.6% |
| 2000 | 98% | 100% |
| 3000 | 99.5% | 100% |
| 4000 | 99.7% | 100% |
| 5000 | 100% | 100% |

Variable Compositional Materials

Most minerals do not have a stoichiometric composition. In general, there is a continuum of compositions which are grouped together and given the name of a single mineral. For example, the mineral feldspar contains a solid solution between three end-members that have stoichiometric compositions. Other minerals may have complicated interrelations between elements that cannot be described completely using a single point definition.

Prior art methods do not address the issue of variable compositional minerals and consequently require an operator to manually create fake mineral definitions for each of the intermediate chemical compositions. In other words, minerals with complex interrelations and variable compositions are given a "fake" definition for each concentration point, and all the "fake" definition points together form all the possible concentrations of the variable mineral. This creates a vast number of possible "minerals" in a database, which has several disadvantages. First, additional training time is required to instruct users on how to work around the limitation of variable compositional definitions. Secondly, additional maintenance time is required for users to create and track the large number of mineral definitions. Thirdly, as users encounter new unknown mineral definitions, they must determine whether they are intermediate mineral compositions or actually new minerals.

One embodiment of the present invention extends the definition of minerals to allow variable compositions and provides a way to compute the nearest point from a variable compositional mineral definition to an observed value. To account for variable composition, a mineral phase definition is represented as two or more mineral definitions linked together to represent end-members of the chemistry of the mineral, and the sub-space in between the end-members represents all valid compositions for a particular mineral. When definitions of the end-members of a mineral are not available, because the pure end-members are rare in nature, intermediate compositions are preferably recorded, along with the theoretical minimum and maximum values for each element in the mineral.

For example, the Plagioclase mineral series can be defined as all compositions between Albite ($NaAlSi_3O_8$) and Anorthite ($CaAl_2Si_2O_8$). Assuming that a composition near Albite is recorded as:

|  | Na | Ca | Al | Si | O |
|---|---|---|---|---|---|
| Concentration | 7.25% | 2.83% | 12.41% | 20.75% | 48.16% |
| Std Deviation | 2.7% | 1.7% | 3.5% | 5.4% | 6.9% |

Assuming that a composition near Anorthite is recorded as:

|  | Na | Ca | Al | Si | O |
|---|---|---|---|---|---|
| Concentration | 1.81% | 11.30% | 17.33% | 22.90% | 46.64% |
| Std Deviation | 1.3% | 3.4% | 4.2% | 4.8% | 6.8% |

The theoretical values for the minimum and maximum concentrations of each element are then preferably defined as:

|  | Na | Ca | Al | Si | O |
|---|---|---|---|---|---|
| Minimum | 0% | 0% | 10.77% | 20.75% | 46.14% |
| Maximum | 9.06% | 14.13% | 18.97% | 31.5% | 48.66% |

An unknown mineral composition can be classified against this definition by finding the point within the definition that is nearest to the point determined by the elemental decomposition of the measured spectrum. This is done by calculating the solution to the constrained linear least-squares problem defined as:

Find x that minimizes $\|Ax-b\|$ subject to $\Sigma x=1$, $C\ x<=d$, where:

the columns of A are the example mineral element concentrations, b is the unknown measured element concentration, $$C = \begin{pmatrix} A \\ -A \end{pmatrix},$$

$$d = \begin{pmatrix} UpperBounds \\ -LowerBounds \end{pmatrix}$$

x will contain the proportions of each example composition, so the nearest composition n will be:

$n = Ax.$

The standard deviations are also linearly interpolated according to the x vector:

$S = Ex$

Where: the columns of E are the standard deviations of the example mineral elements, And s is the standard deviations of the elements in the nearest valid composition n.

For the Plagioclase example described above, the calculations indicate the following results:

$$A = \begin{pmatrix} 7.25 & 1.81 \\ 2.83 & 11.30 \\ 12.41 & 17.33 \\ 20.75 & 22.90 \\ 48.16 & 46.64 \end{pmatrix}$$

$$C = \begin{pmatrix} 7.25 & 1.81 \\ 2.83 & 11.30 \\ 12.41 & 17.33 \\ 20.75 & 22.90 \\ 48.16 & 46.64 \\ -2.83 & -11.30 \\ -12.41 & -17.33 \\ -20.75 & -22.90 \\ -48.16 & -46.64 \end{pmatrix}$$

$$d = \begin{pmatrix} 9.06 \\ 14.13 \\ 18.97 \\ 31.50 \\ 48.66 \\ 0 \\ 0 \\ -10 \end{pmatrix}$$

Those skilled in the art will readily appreciate that this type of constrained least-squares equations can be solved effectively. For the plagioclase example, assume that an unknown elemental composition is measured, such that:
b={Na=8.6%, Ca=0.4%, Al=11%, Si=31.0%, O=49.0%}
Using the constrained least squares solver, the output becomes $$x = \begin{pmatrix} 1.2759 \\ -0.2759 \end{pmatrix},$$

and nearest composition $$n = A$$

$$x = \begin{pmatrix} 8.7478 \\ 0.4869 \\ 11.0526 \\ 31.1296 \\ 48.5732 \end{pmatrix}$$

with standard deviations $$s = E$$

$$x = \begin{pmatrix} 3.0636 \\ 1.2173 \\ 3.3462 \\ 5.5920 \\ 6.9697 \end{pmatrix}$$

Once the nearest composition is found as described above, the mineral can be identified according the method described in FIG. 5. That is, a distance is determined between the closest point in the subspace from each of multiple mineral definitions and the unknown mineral. Thus, an embodiment of the present invention allows for a mineral definition with multiple disconnected mineral series for minerals like feldspars, which have multiple disconnected elements.

In the example described above, the "endpoints" of the mineral definition subspace are defined by the elemental concentration in the two minerals, Albite and Anorthite, each of which includes at least 4 elements.

Figure 14:
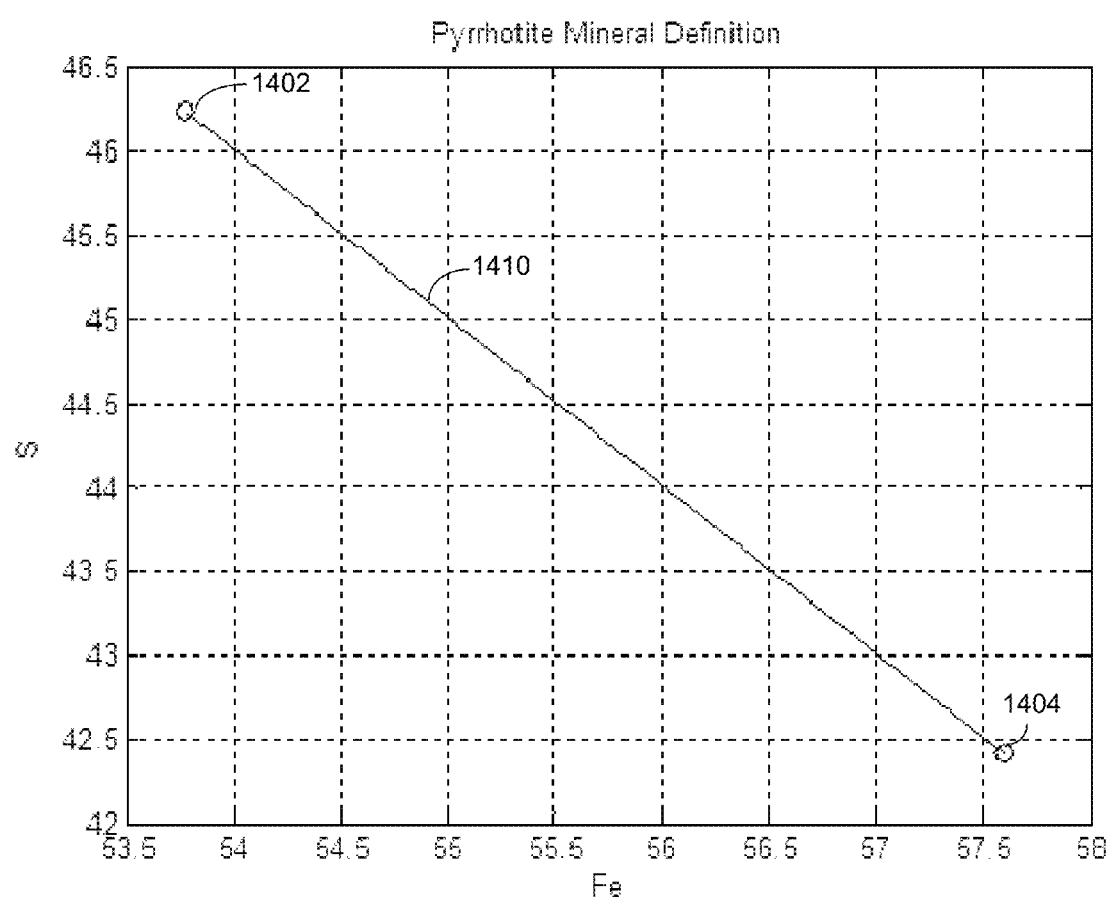
FIG. 14 shows an example definition of the mineral pyrrhotite according to an embodiment of the present invention.

FIG. 14 shows simpler, more easily visualized, mineral system in which a mineral definition of pyrrhotite includes a range of two elements, iron and sulfur. All possible combinations from zero to 100% for iron and for sulfur comprise an element space. The subset of the element space that is included in the mineral definition comprises a subspace 1410 having two end members 1402 and 1404. Any point on the sub-space 1410 is considered to be a valid definition for the mineral pyrrhotite. That is, the entire element space is represented by a line that passes through end points 1402 and 1404, and the sub-space of the mineral definition comprises the line segment between the end points. The mineral definition, instead of being a single point, is thus extended to contain a specified range of concentration values. The compositional ranges that comprise the definition can be set, for example, by either using theoretical end values or by using experimental end values from measured known minerals.

Figure 15:
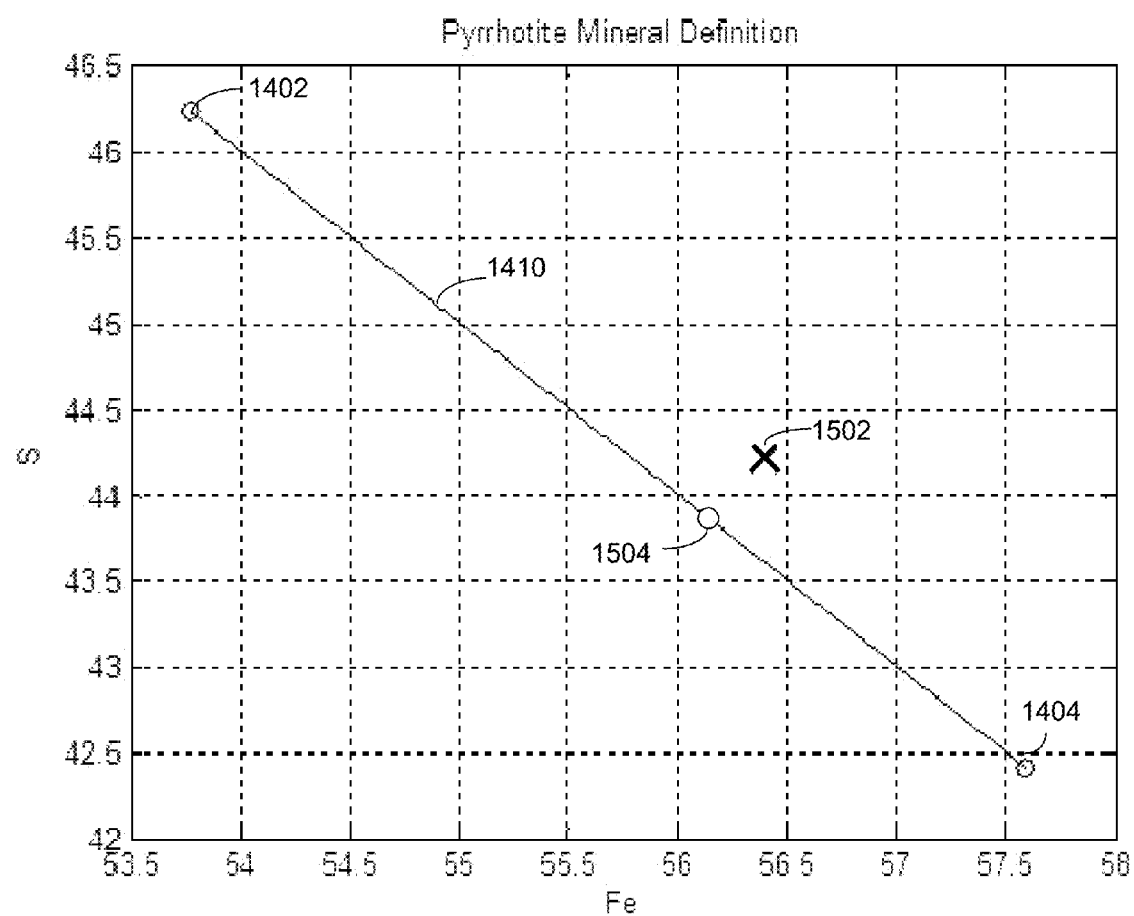
FIG. 15 shows the variable pyrrhotite mineral definition again, with a point representing an example computed value obtained for Fe and S after performing elemental decomposition of an x-ray spectrum of an unknown sample.

FIG. 15 shows the subspace defining the mineral pyrrhotite again, with an experimentally acquired point 1502 representing the concentrations of Fe and S determined after performing elemental decomposition of an x-ray spectrum of an unknown sample. Even if the unknown sample contains pyrrhotite, the elemental quantification will typically result in a point that is not exactly on the line because the spectra is acquired quickly using a relatively low number of counts and a relatively low signal-to-noise ratio. According to one embodiment of the invention, the closest point in the mineral definition is calculated by projecting the point 1502 onto the sub-space 1410. The closest point within the subspace 1410 to the measured point 1502 is labeled as point 1504 in this case. After the closest point within the subspace is determined, a similarity metric can be calculated to compare how close the unknown mineral is to the point 1504 in the mineral definition subspace. A probability value can be calculated to determine the probability that the unknown sample is composed of the mineral corresponding to the mineral definition.

In some embodiments, the subspace is extended if proper criteria are met. This allows the mineral definition of a limited range to be extended to include the minerals that have similar interactions between elements. This is extremely useful because the possibility of measuring all elements and all their corresponding end members is very unlikely. However, over time, as more and more samples are measured, these definitions can be grown and extended to better represent their true end members.

Figure 16:
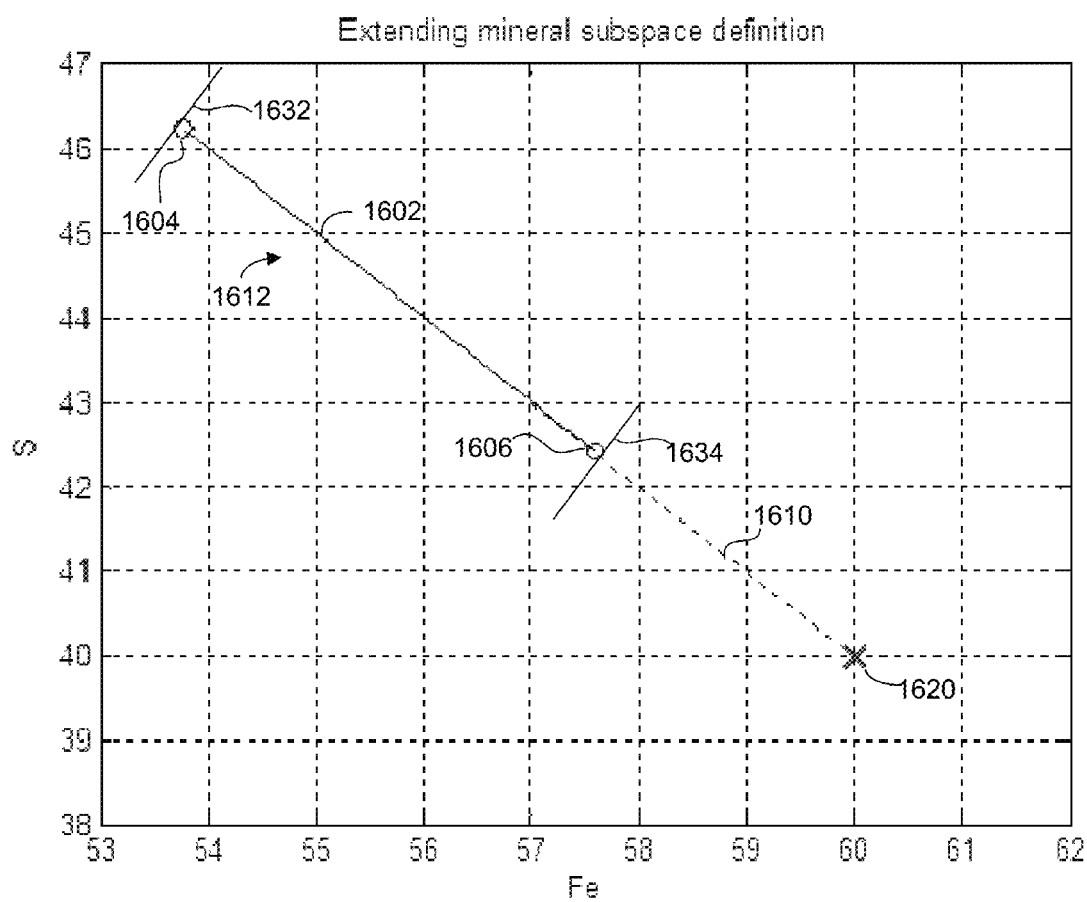
FIG. 16 shows an example of a scenario according to an embodiment of the present invention when a computed value lies on the same line but outside of the sub-space bounds of a mineral definition.

FIG. 16 shows an example of the situation in which when a computed compositional value 1620 of the unknown mineral lies on the same line, but outside of the sub-space that bounds the mineral definition, that is, on the line, but not on the bounded line segment. Subspace 1602 is defined by end members 1604 and 1606, and sub-space bounds 1612 is the area or volume between perpendicular projections 1632 and 1634 to the subspace 1602 at the end members. The computed value 1620 for a measured spectrum lies outside of the subspace bounds, but the point 1620 fits very closely to an extrapolation 1610 of the sub-space. If the distance between the computed value 1620 and the extrapolation 1610 lies within a certain user-defined threshold, the sub-space 1602 can be extended to include point 1620 itself or the point in the extrapolation 1610 closest to point 1620 within the certain threshold.

Figure 17:
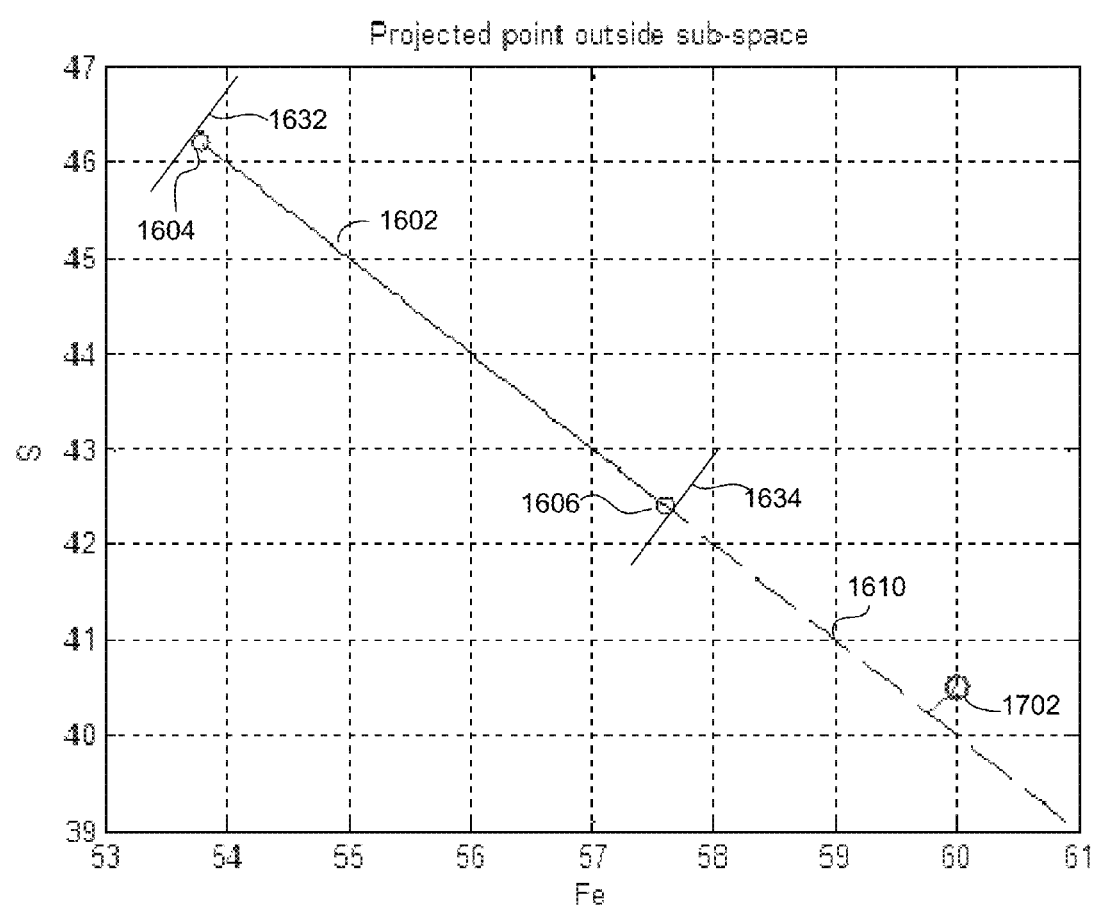
FIG. 17 is another example of a scenario when computed value 1802 lies outside the subspace bounds of a mineral definition.

FIG. 17 is an example of when the projection of the computed value 1702 onto the line lies outside the subspace bounds of a mineral definition and when the distance from the point 1702 to the line exceeds the user defined threshold. In this case, the subspace 1602 is not extended, and end member 1606 is used as the closest point of subspace 1602 to the computed value 1702. The distance metric or probability is then determined, as described in FIG. 5, between end member 1606 and point 1702.

Figure 18:
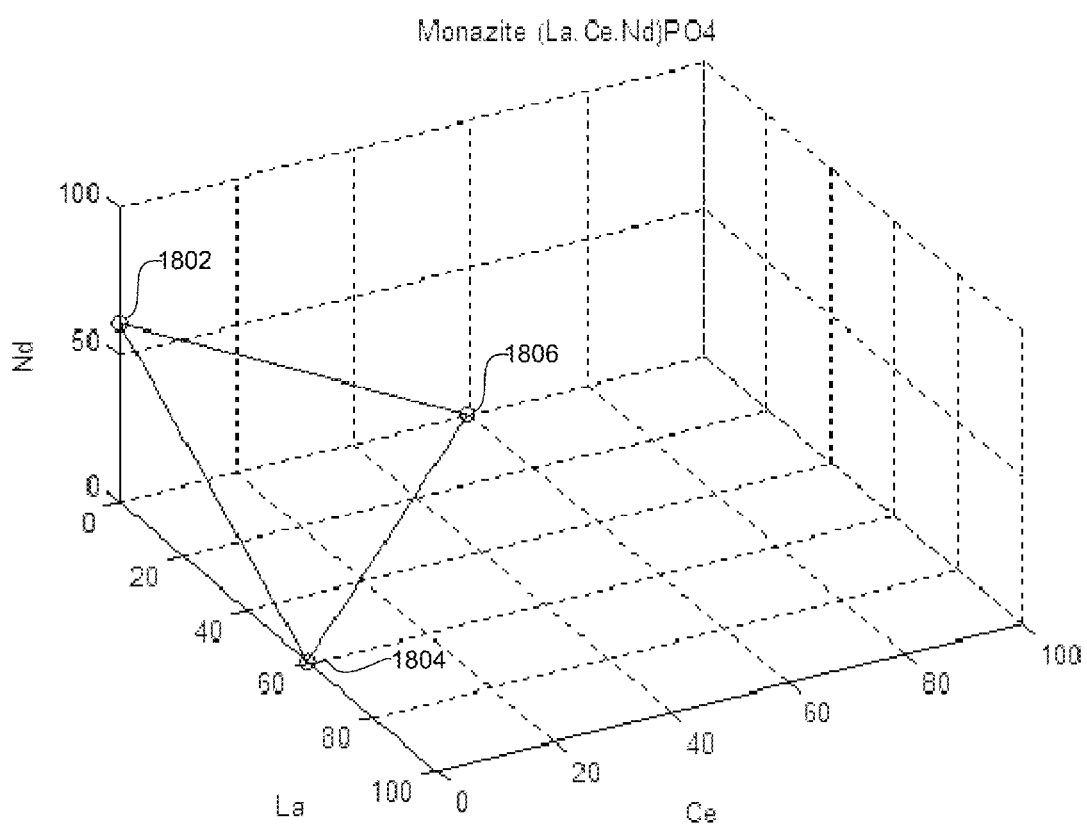
FIG. 18 shows an example of a graph that shows a three element substitution for La, Ce and Nd for one phase of the rare earth mineral Monazite.

FIG. 18 shows an example of a graph that shows a three element substitution for La, Ce and Nd for one phase of the rare earth mineral Monazite. In this particular example, end members 1802, 1804, and 1806 define a subspace 1810 that defines all valid compositions for elements (Nd, La, and Ce) in Monazite. In certain embodiments, the subspace representing valid concentrations for a particular mineral will be a plane or other geometric shape.

FIG. 19 is a flowchart 1900 showing the steps of an embodiment of the present invention in which the composition of an unknown mineral is determined using a mineral definition having a range for at least on element. Step 1902 includes defining minerals with variable compositions and storing them into a database. Mineral definitions may be obtained from high quality spectra having more than 10,000 x-ray counts, more than 100,000 counts or more than 1,000,000 counts, each spectrum may be measured multiple times. Alternatively, mineral definitions can be derived from pre-established standard definitions. The definitions may include standard deviation, count, and backscatter intensity values as explained in FIG. 5. Step 1904 then includes acquiring a spectrum of an unknown sample, typically using less than 10,000 x-ray counts, less than 5,000 counts, less than 2,000 counts, and preferably about 1,000 counts.

Step 1906 includes decomposing the spectra of the unknown mineral according to the methods described above. Decomposing the spectra preferably includes splitting the spectra into segments representing peaks and then performing a curve-fitting with elemental spectra of the mineral definitions using the least squares method. Step 1908 includes selecting a mineral definition from the database. Conditional step 1910 then determines if the computed value from the decomposed spectra of the unknown sample is within the subspace bounds of the selected mineral definition. If the computed value is within the subspace bounds, the method proceeds with step 1912, in which the closest point to the computed value within the subspace is calculated. If the computed value is not within the subspace bounds, then conditional step 1914 determines if the extrapolation of the subspace will result in the computed value being within a certain user defined threshold. If the distance between the computed value and the extrapolation of the subspace is not within a user defined threshold, the method proceeds with step 1912 of calculating the closes point in the existing subspace. If the probability between the computed value and the extrapolation is within a user defined threshold, then step 1916 includes extending the subspace such that the definition of the selected mineral now includes the projection of the computed value. This step of extending the definition of a mineral can be done automatically. Step 1918 then calculates the mineral probability or other similarity metric, either by established prior art methods or by the methods described in FIG. 5.

After testing one mineral definition to determine a probability, the system continues to test additional mineral definitions until all mineral definitions are tested. In step 1920, the system determines if any mineral definitions are left to be tested and, if so, selects the next mineral definition in step 1908 and repeats the process of determining a probability of a match. Once all the mineral definitions have been compared to the computed value, step 1922 includes identifying the mineral, typically as the mineral having the highest probability or best similarity metric above a threshold value. The method preferably displays the probability the mineral match and can display the probability values for all minerals the computed value was compared to.

Certain embodiments of this invention thus allow for resolving boundary phases between minerals. These embodiments allow a mineral definition to be constructed instantly between real minerals to create a virtual mineral that mixes the compositions of two or more minerals. By using this approach for defining minerals, mineral definitions for boundary phases can be automatically created without having to manage them explicitly as in the prior art.

In some embodiments, the use of elemental information is hidden from the operator, and the concept of re-computing the match statistics based on the number of x-ray photons in the spectrum is automatic. In the prior art, the mineral definitions are tied to the number of x-rays being measured.

In some embodiments, the system supports minerals that have non fixed compositions directly. Almost all minerals in nature have variability in their composition, and these are not accommodated in prior art QEMSCAN or MLA systems. The operator is forced to create intermediate mineral definitions for these cases, which significantly adds to their workload to create and maintain a series of intermediate definitions. And when a pixel contains a mixture of minerals (as happens for almost all pixels in shale), the number of possible combinations becomes prohibitive to maintain manually.

Some portions of the description are explicitly or implicitly presented in terms of algorithms and functional or symbolic representations of operations on data within a processor or a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the prior descriptions, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

Thus, the present specification discloses both a method and an apparatus for performing the operations of the method. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

Although much of the previous description is directed at semiconductor wafers, the invention could be applied to any suitable substrate or surface. Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . ."

To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of determining the mineral present at a point in a sample of unknown composition, comprising:
   directing an electron beam toward a point on the sample to acquire an x-ray spectrum;
   providing a mineral definition for a first mineral, the mineral definition for the first mineral including a list of elements comprising the first mineral, each of the elements having a corresponding standard spectrum associated with the first mineral, the combination of the standard spectra associated with the first mineral forming a first combined standard spectrum;
   providing a mineral definition for a second mineral, the mineral definition for the second mineral including a list of elements comprising the second mineral, each of the elements having a corresponding standard spectrum associated with the second mineral, the combination of the standard spectra associated with the second mineral forming a second combined standard spectrum;
   comparing the acquired spectrum from the point on the sample to the first combined standard spectrum of the elements from the element list of a first mineral definition;
   comparing the acquired spectrum from the point on the sample to the second combined standard spectrum of the elements from the element list of a second mineral definition;
   determining whether the first combined standard spectrum or the second combined standard spectrum best matches the acquired spectrum;
   classifying the point on the sample as being composed of the first mineral if the first combined standard spectrum matches the acquired spectrum better than the second combined standard spectrum; and
   classifying the point on the sample as being composed of the second mineral if the second combined standard spectrum matches the acquired spectrum better than the first combined standard spectrum.

2. The method of claim 1 in which comparing the spectrum of the unknown mineral sample to the combined spectra of the elements from each mineral definition includes splitting elemental standard spectra into segments and individually fitting segments of the acquired spectrum of the sample to segments of the elemental standard spectra.

3. The method of claim 2 in which the multiple segments correspond to multiple peaks in the standard spectra.

4. The method of claim 1 in which comparing the spectrum of the unknown mineral sample to the combined spectra of the elements from each mineral definition includes calculating an overall probability match between the sample and the combined spectra of the elements from each mineral definition.

5. The method of claim 1 in which calculating an overall probability for the unknown mineral sample to the mineral definition includes determining an average backscattered electron value and standard deviation for the multiple known samples of a mineral and comparing said average backscattered electron value and standard deviation to a backscattered electron value of the unknown mineral sample.

6. The method of claim 1 comparing the spectrum of the unknown mineral sample to the combined spectra of the elements from each mineral definition includes computing a nearest point in the mineral definition to values from the decomposed spectrum.

7. A system for spectrum data analysis, comprising:
an electron beam column for directing an electron beam toward a sample;
an x-ray spectrometer for measuring the energy of x-rays emitted from the sample in response to the electron beam;
a processor for executing computer instructions to analyze a mineral sample; and
a computer memory for storing instructions for carrying out the method of claim 1.

8. A method of spectrum data analysis, the method comprising:
acquiring a spectrum of an unknown mineral sample;
selecting a first mineral definition, the first mineral definition including an element list of the elements comprising the first mineral;
decomposing the spectrum of the unknown mineral sample using elements from the first mineral definition;
calculating an overall match probability between the unknown mineral sample and the first mineral definition; and
selecting a second mineral definition, the second mineral definition including an element list of the elements comprising the second mineral;
decomposing the spectrum of the unknown mineral sample using elements from the second mineral definition;
calculating an overall match probability between the unknown mineral sample and the second mineral definition; and
in response to the first mineral definition having a greater match probability than the second mineral definition, classifying the acquired spectrum as being composed of the first mineral; and
in response to the second mineral definition having a greater match probability than the first mineral definition, classifying the acquired spectrum as being composed of the second mineral.

9. The method of claim 8, further comprising computing a nearest point in the mineral definition to values from the decomposed spectrum.

10. The method of claim 8, further comprising displaying the overall probability for a user to review.

11. The method of claim 8, further comprising:
creating a mineral definition by measuring multiple known samples of a mineral; and
storing the definition in a database.

12. The method of claim 11 in which the step of creating a mineral definition by measuring multiple known samples of a mineral is repeated multiple times to create multiple mineral definitions.

13. The method of claim 8 in which calculating an overall probability for the unknown mineral sample to the mineral definition includes determining an average backscattered electron value and standard deviation for the multiple known samples of a mineral and comparing said average backscattered electron value and standard deviation to a backscattered electron value of the unknown mineral sample.

14. The method of claim 8, in which decomposing the spectrum of the unknown mineral sample using elements from the selected element list includes obtaining elemental spectra for the mineral definition selected and splitting the elemental spectra into segments based on the number of peaks present in the spectrum of the unknown mineral sample.

15. The method of claim 14, in which splitting the spectrum into segments includes splitting the spectrum into regions around known peak energies.

16. The method of claim 8, in which decomposing the spectrum of the unknown mineral sample includes performing a curve fitting of the elemental spectra to the spectrum of the unknown mineral sample.

17. The method of claim 16 in which performing a curve fitting of elemental spectra includes a linear decomposition.

18. The method of claim 8 in which computing a nearest point in the mineral definition to values from the decomposed spectrum includes a least squares method to determine the minimum distance from the values from the decomposed spectrum to the nearest point in the mineral definition.

19. The method of claim 8 in which calculating an overall probability match for the unknown mineral sample to the mineral definition includes calculating individual element probability matches from the decomposed spectrum to the mineral definition and calculating an overall similarity metric by multiplying the individual element probability matches.

* * * * *